(12) United States Patent  
Zhang

(10) Patent No.: US 9,499,586 B2
(45) Date of Patent: Nov. 22, 2016

(54) ANTICANCER AND ANTI-OBESITY CYCLIC PEPTIDE AGENTS

(71) Applicant: Hong Kong Baptist University, Kowloon (HK)

(72) Inventor: Hongjie Zhang, Kowloon (HK)

(73) Assignee: Hong Kong Baptist University, Hong Kong (HK)

( * ) Notice: Subject to any disclaimer, the term of this patent is extended or adjusted under 35 U.S.C. 154(b) by 342 days.

(21) Appl. No.: 13/804,276

(22) Filed: Mar. 14, 2013

(65) Prior Publication Data

US 2014/0107018 A1    Apr. 17, 2014

Related U.S. Application Data

(60) Provisional application No. 61/795,443, filed on Oct. 16, 2012.

(51) Int. Cl.
| | |
|---|---|
| A61K 38/00 | (2006.01) |
| C07K 7/00 | (2006.01) |
| C07K 7/64 | (2006.01) |
| C07K 11/02 | (2006.01) |

(52) U.S. Cl.
CPC ........ *C07K 7/64* (2013.01); *C07K 11/02* (2013.01)

(58) Field of Classification Search
None
See application file for complete search history.

(56) References Cited

PUBLICATIONS

An et. al. ph-(low)-insertion-peptide (pHLIP) translocation of membrane impermeable phalloidin toxin inhibits cancer cell proliferation, PNAS Nov. 23, 2010, vol. 107, No. 47, 20247.*
Lacroix et. al. Unprecedented Occurrence of Isoaspartic Acid in a Plant Cyclopeptide, Organic Letters vol. 14, No. 2, 2012, Published on Web Jan. 5, 2012, 576-579).*
Kinghorn et.al., Curr Opin Drug Discov Devel. Mar. 2009 ; 12(2): 189-196.*
Global Plants, Maytenus variabilis, JSTOR, http://plants.jstor.org/stable/10.5555/al.ap.specimen.k000669798).*
D. Ma et. al. Tetrahedron 56 (2000) 7447-7456.*
Medline Plus, Obesity, http://www.nlm.nih.gov/medlineplus/obesity.html , Dec. 10, 2015.*
St. John Providence Health Center; Preventing Obesity, http://www.stjohnprovidence.org/HealthInfoLib/swArticle.aspx?85,P0786 Dec. 10, 2015.*
Overview of Leukemia at URL merckmanuals.com/home/blood_disorders/leukemias/overview of leukemia.html?qt=Leukemia &alt=sh accessed Aug. 20, 2014.*
National Institute of Cancer—understanding cancer and related topics, accessed Aug. 21, 2014 at U RL: cancer.aovlcancertonics/understandinacancer.*
Merck Manual Colorectal Cancer accessed Aug. 21, 2014 at U RL merckmanuals.com/home/digestive_disorders/tumors of the_digestive_system/colorectal_cancer.html).*
Merck Manual Breast Cancer accessed Aug. 21, 2014 at URL: merckmanuals.com/home/womens health_issues/breast_disorders/breast_cancer.html.*
Merck Manual Prostate Cancer accessed Aug. 21, 2014 at U RL: merckmanuals.com/home/kidney_and_urinary_tract_disorders/cancers of the kidney_and_genitourinary_tract/prostate_cancer.html?qt=prostate cancer&alt=s.*
Merck Manual Bladder Cancer accessed Aug. 21, 2014 at URL: merckmanuals.com/home/kidney_and urinary_tract_disorders/cancers of the kidney_and_genitourinary_tract/bladder_cancer.htm.*
Merck Manual Cancer of the Uterus, accessed Aug. 21, 2014 at URL: merckmanuals.com/home/womens_health_issues/cancers of the female_reproductive_system/cancer of the uterus.html?qt=Cancer of the Uterus&alt=s.*
Ovarian Cancer, accessed Aug. 21, 2014 at merckmanuals.com/home/womens_health_issues/cancers_of_the_female_reproductive_system/ovarian_cancer.html?qt=ovarian cancer&alt=sh.*

(Continued)

*Primary Examiner* — Jeanette Lieb
(74) *Attorney, Agent, or Firm* — Renner Kenner Greive Bobak Taylor & Weber

(57) ABSTRACT

A compound having formula (I) or formula (II):

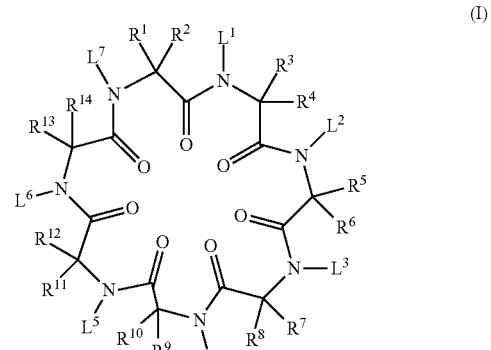

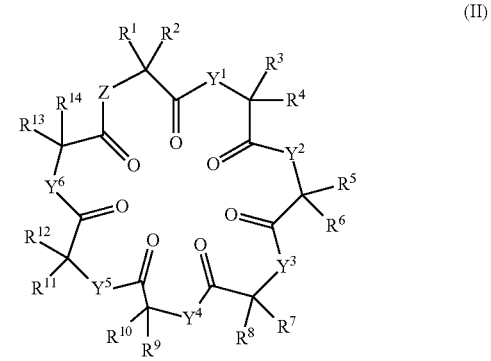

for use in anticancer or anti-obesity.

4 Claims, 23 Drawing Sheets

(56) References Cited

PUBLICATIONS

World Health Organization Media Center, "Cancer", Fact Sheet N°297, Reviewed Jan. 2013.
World Health Organization Media Center, "Obesity and overweight", Fact Sheet N°311, Updated Mar. 2013.
Jutiviboonsuk, Aranya, et al.; "Bioactive constituents from roots of Bursera tonkinensis"; Phytochemistry 66; (2005); 2745-2751.
Tan, Ning-Hua & Zhou, Jun; "Plant Cyclopeptides"; Chemical Reviews, 2006, vol. 106, No. 3, 840-841.
Feng, Yunjiang, et al.; "Two Novel Cytotoxic Cyclodepsipeptides from a *Mycoparasitic cladobotryum* sp."; J. Org. Chem, vol. 68, No. 5, 2003, 2002-2003.
Zhang, Hong-Jie et al.; "Miliusanes, A Class of Cytotoxic Agents from Miliusa sinensis"; Journal of Medicinal Chemistry, 2006, vol. 49, No. 2, 693-708.
Chatterjee, Jayanta et al.; "N-Methylation of Peptides: A New Perspective in Medicinal Chemistry"; Accounts of Chemical Research, vol. 41, No. 10, Oct. 2008, 1331-1342.
Shimokawa, Kenichiro et al.; "(_)-Ternatin, a highly N-methylated cyclic heptapeptide that inhibits fat accumulation: structure and synthesis"; Tetrahedron Letters 47 (2006) 4445-4448.

\* cited by examiner

ANTICANCER AND ANTI-OBESITY CYCLIC PEPTIDE AGENTS

CROSS-REFERENCE TO RELATED APPLICATION

The present application claims priority of U.S. provisional application No. 61/795,443 filed Oct. 16, 2012, the content of which is incorporated herein by reference in its entirety.

FIELD OF INVENTION

This invention relates to a compound for anticancer and anti-obesity, and particularly, but not exclusively, a compound based on cyclic peptide agents for anticancer and anti-obesity.

BACKGROUND OF INVENTION

More than 10 million people are diagnosed with cancer every year in the world. Cancer has become a leading cause of death, accounting to about 13% of all deaths. According to the compiled statistics by WHO, cancer claimed the lives of more than 7.6 million people worldwide in 2008 (WHO: http://www.who.int/mediacentre/factsheets/fs297/en/index.html; retrieved on 12, Oct., 2012). It is estimated that the annual death toll will reach 13.1 million by 2030. Although numerous cancer chemotherapeutics are available today, they often have very narrow therapeutic indices and very severe side effects. In addition, cancers can and often do develop resistance to many of these drugs. The fact that there currently are no drugs available that are capable of curing cancer diseases, the discovery and development of new anticancer drugs are very much needed and the undertaking of such studies is imperative.

Obesity has become increasingly concerned in modern society. It affects nearly a third population of adults in the developed countries, and more than 1.4 billion adults were overweight in 2008 according to WHO report (http://www-.who.int/mediacentre/factsheets/fs311/en/, retrieved on 14 Oct., 2012.). Many health problems such as cardiovascular diseases, type 2 diabetes, cancer and osteoarthritis are associated with obesity. Obesity is largely preventable, and in fact, it is considered to be a leading preventable cause of death in the world. However, the number of people with obesity in the world is more than doubled since 1980. Obesity, the once considered a wealthy country problem is now on the rise in low- and middle-income countries. Therefore, in many cases, treatment may become inevitable option. There is only one anti-obesity drug (orlistat) approved by the FDA for long term use. The drug has side effects associated with high blood pressure, rapid heart eat, palpitations, drug addiction, and insomnia. To develop new anti-obesity drugs is thus needed.

Cyclopeptides (cyclic peptide) are peptide compounds whose amino and carboxyl termini are linked together by a peptide bond to form a circular chain. Cyclodepsipeptides have at least one lactone linkage in place of one of the amides. A cycloheptapeptide is the cyclopeptide compound containing seven amino acid residues.

A large number of cyclopeptides have been synthesized due to their variety of biological activities including anticancer activity (Wessjohann L A, Andrade C K, Vercillo O E, Rivera D G. Macrocycli peptoids: N-alkylated cyclopeptides and depsipeptides). Many cyclopeptides have also been reported from plants (Tan N H & Zhou J. Plant cyclopeptides. Chemical Review 2006; 106: 840-895). However, cyclopeptides containing rare amino acids are seldom reported either from synthetic study or from nature. We have discovered novel plant cyclopeptides that contain a unique amino acid residue in the structure.

Citation or identification of any reference in this section or any other section of this application shall not be construed as an admission that such reference is available as prior art for the present application.

SUMMARY OF INVENTION

The present invention is based, at least in part, on the discovery that cyclopeptide compounds such as compound 1 below isolated from the dry stem barks of the decayed woods of the plant *Maytenus variabilis* (Loes.) C. Y. Cheng (Celastraceae) are effective in the treatment of cancer and obesity diseases.

Accordingly, a first aspect of the invention is a cycloheptapeptide compound or a pharmaceutically acceptable salt or pro-drug thereof, for use in the treatment, prevention or delay of progression of a cancer or an obesity in a patient. The cycloheptapeptide may be a cyclohepta-depsipeptide compound.

A second aspect of the invention is a pharmaceutical formulation comprising a cycloheptapeptide compound, or a pharmaceutically acceptable salt or pro-drug thereof, for use in the treatment, prevention or delay of progression of a cancer or an obesity in a patient. The cycloheptapeptide may be a cyclohepta-depsipeptide compound.

A third aspect of the invention concerns the use of a combination of one or more cycloheptapeptide(s) based on the formula (I) or the formula (II) below with one or more other clinically used anticancer or anti-obesity agent(s), for use in the treatment, prevention or delay of progression of a cancer or an obesity in a patient.

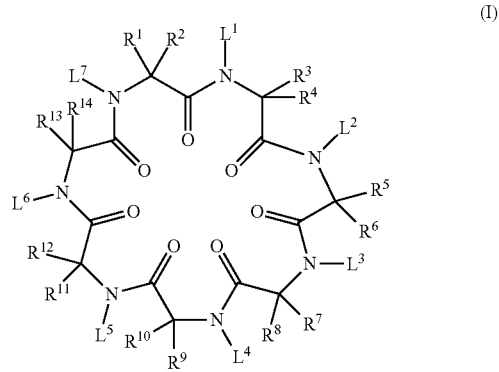

(I)

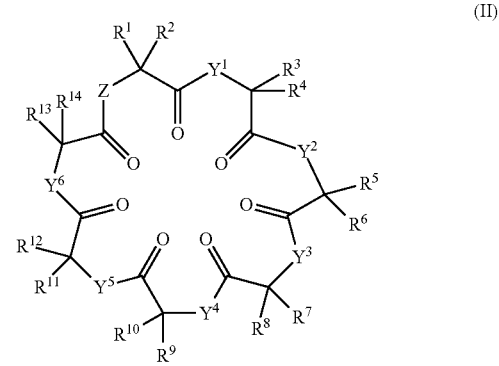

(II)

A fourth aspect of the invention concerns the use of an extract or a fraction made from plant material or extraction material fermented from a microorganism containing one or more cycloheptapeptide(s) based on the formula (I) or the formula (II) for use in the treatment, prevention or delay of progression of a cancer or an obesity in a patient.

Another aspect of the invention concerns an amide or amine that contains at least one substructure that is formed from the amino acid having the formula (III).

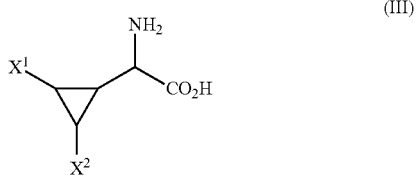

(III)

Compounds of the invention may exist in different forms, such as free acids, free bases, enantiomers, esters and other prodrugs, salts and tautomers, for example, and the disclosure includes all variant forms of these compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages, which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The present invention will become apparent from the following description, when taken in conjunction with the accompanying drawings, in which.

DETAILED DESCRIPTION OF THE INVENTION

Figure 1A:
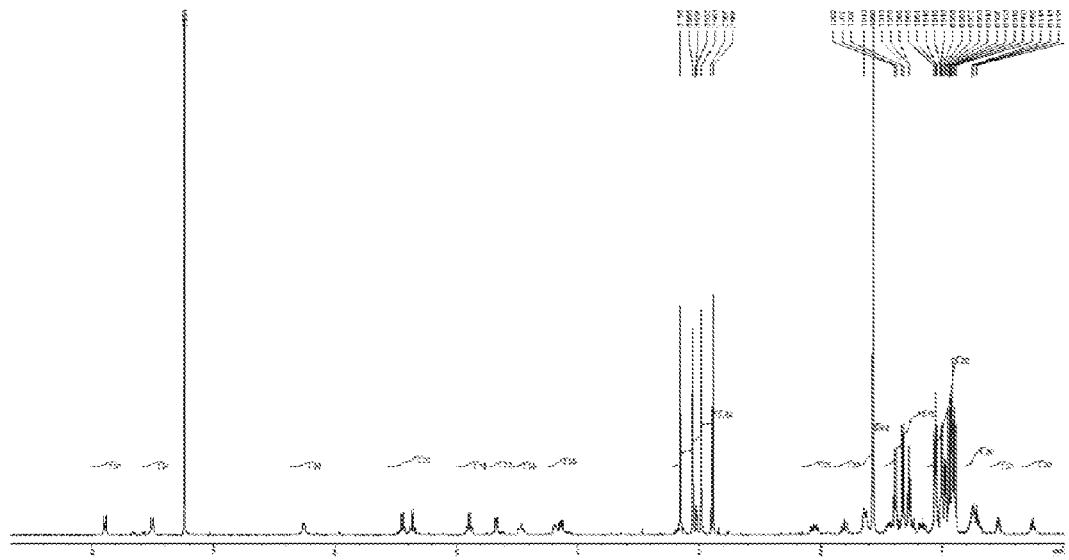
FIG. 1(A) shows $^1$H NMR data of 1 (CDCl$_3$).

In our continuing drug discovery program, we have discovered potent anticancer and anti-obesity compounds from a plant. The promising compounds belong to cyclopeptides containing a novel amino acid residue, and they were isolated from the stem barks of *Maytenus variabilis*

(Loes.) C. Y. Cheng (Celastraceae). The novel cyclopeptide compounds (1, 2 and 3) demonstrated tumor cell killing activity against a panel of human cancer cell lines with $IC_{50}$ values in the range of 0.05-52 nM. Compound 1 also demonstrated to be effective on reducing body weight of mice.

The present invention is not to be limited in scope by any of the specific embodiments described herein. The following embodiments are presented for exemplification only.

Cycloheptapeptide Compound

The term "cycloheptapeptide" as used herein includes reference to a cyclopeptide compound whose amino and carboxyl termini are linked together by a peptide bond to form a circular chain. A cycloheptapeptide comprises the basic structure shown as below:

1
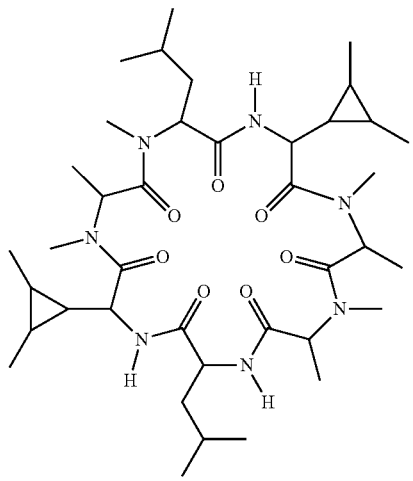

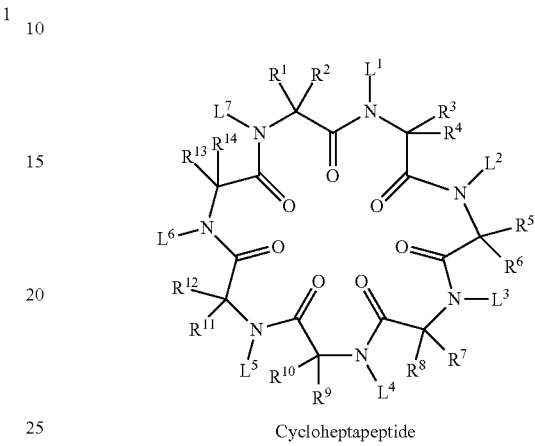
Cycloheptapeptide

The term "cyclohepta-depsipeptide" as used herein includes reference to a cyclodepsipeptide compound, which has at least one lactone linkage in place of one of the amides. A cyclohepta-depsipeptide comprises the basic structure shown as below:

2
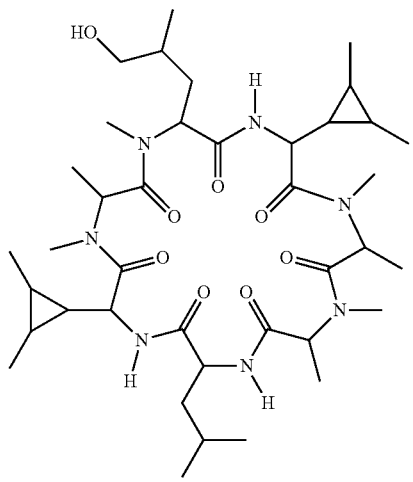

3
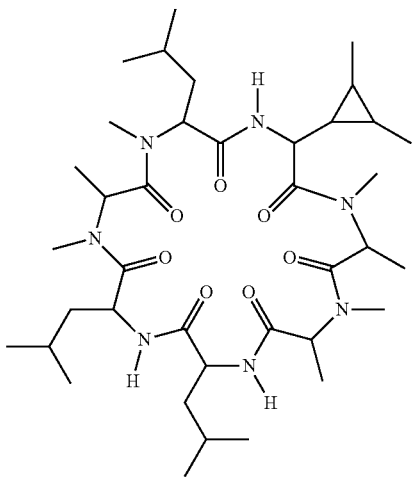

Cyclohepta-depsipeptide $Y^1$, $Y^2$, $Y^3$, $Y^4$, $Y^5$, and $Y^6$ can be oxygen, sulfur or nitrogen substituted with an L group (L can be $L_1$, $L_2$, $L_3$, $L_4$, $L_5$ or $L_6$). T can be a hydrocarbyl or an alkoxy. At least one of the $Y^1$, $Y^2$, $Y^3$, $Y^4$, $Y^5$ and $Y^6$ is nitrogen.

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

Cyclic "group" means a ring or ring system, which may be unsaturated or partially unsaturated but is usually saturated, typically containing 5 to 13 ring-forming atoms, for example a 3, 4-, 5- or 6-membered ring. The ring or ring system may be substituted with one or more hydrocarbyl groups. Cyclic group includes carbocyclyl and heterocyclyl moieties.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 3-, 4-, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, (β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Amino Acid

The term "amino acid" as used herein includes reference to a compound comprising the basic structure shown as below:

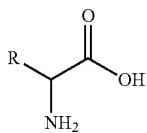

R is selected from $R^1$, —$OR^1$, —$C(O)R^1$ and —$C(O)OR^1$;

$R^1$ is independently selected from hydrogen, halogen, trifluoromethyl, cyano, nitro, hydrocarbyl optionally substituted with 1, 2, 3, 4 or 5 $R^2$, —$(CH_2)_k$-heterocyclyl optionally substituted with 1, 2, 3, 4 or 5 $R^2$, —$OR^3$, —$C(O)R^4$, —$C(O)N(R^3)R^4$, —$C(O)OR^3$, —$OC(O)R^3$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^2$ is independently selected from halogen, trifluoromethyl, cyano, nitro, oxo, =$NR^3$, —$OR^3$, —$C(O)R^4$, —$C(O)N(R^3)R^4$, —$C(O)OR^3$, —$OC(O)R^4$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^3$ and $R^4$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3);

The nitrogen atom of the amino acids may be alkylated to form N-alkylated amino acids. The amino acids can be L-amino acids, or D-enantiomers of all of the above. An amino acid is, for example, selected from twenty genetically encoded L-amino acids (Table 1), common non-encoded amino acids (Table 1), and the like. It also includes α-amino-cyclic-acetic acids (see below the term "α-Amino-cyclic-acetic acid").

TABLE 1

Genetically encoded L-amino acids
and common non-encoded amino acids

| Amino Acid | Common Abbreviation |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |

TABLE 1-continued

Genetically encoded L-amino acids
and common non-encoded amino acids

| Amino Acid | Common Abbreviation |
|---|---|
| Proline | Pro |
| Serine | Ser |
| Threonine | Thr |
| Tryptophan | Trp |
| Tyrosine | Tyr |
| Valine | Val |
| β-Alanine | bAla |
| 2,3-Diaminopropionic | Dpr |
| α-Aminoisobutyric acid | Aib |
| N-Methylglycine (sarcosine0 | MeGly |
| Ornithine | Orn |
| Citrulline | Cit |
| t-Butylalanine | t-BuA |
| t-Butylglycine | t-BuG |
| N-Methylisoleucine | MeIle |
| Phenylglycine | Phg |
| Cyclohexylalanine | Cha |
| Norleucine | Nle |
| 2-Naphthylalanine | 2-Nal |
| 4-Chlorophenylalanine | Phe(4-Cl) |
| 2-Florophenylalanine | Phe(2-F) |
| 3-Florophenylalanine | Phe(3-F) |
| 4-Florophenylalanine | Phe(4-F) |
| Penicillamine | Pen |
| 1,2,3,4-tetrahydroisoquinoline-3-carboxylic acid | Tic |
| β-2-Thienylalanine | Thi |
| Methionine sulfoxide | MSO |
| Homoarginine | hArg |
| N-Acetyl lysine | AcLys |
| 2,4-Diamino butyric acid | $A_2Bu$ |
| p-Aminophenylalanine | Phe(pNH$_2$) |
| N-Methylvaline | MeVal |
| Homocysteine | hCys |
| Homoserine | hSer |
| 2,3-Diaminobutyric acid | DBU |

α-Amino-cyclic-acetic acid

The term "α-amino-cyclic-acetic acid" as used herein includes reference to a compound comprising the basic structure shown as below:

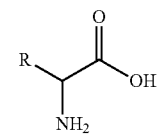

R is selected from cyclic group and —$(CH_2)_k$-cyclic group, either of which is optionally substituted with 1, 2, 3, 4 or 5 substituents independently selected from $R^1$, —$OR^2$, —$C(O)R^3$, —$C(O)N(R^2)R^3$, —$C(O)OR^2$, —$OC(O)R^2$, —$S(O)_2R^2$, —$S(O)_2N(R^2)R^3$, —$N(R^2)R^3$, —$N(R^2)N(R^2)R^3$, —$N(R^2)C(O)R^3$ and —$N(R^2)S(O)_2R^3$;

$R^1$ is independently selected from halogen, trifluoromethyl, cyano, nitro, oxo, =$NR^2$, —$OR^2$, —$C(O)R^3$, —$C(O)N(R^2)R^3$, —$C(O)OR^2$, —$OC(O)R^3$, —$S(O)_2R^2$, —$S(O)_2N(R^2)R^3$, —$N(R^2)R^3$, —$N(R^2)N(R^2)R^3$, —$N(R^2)C(O)R^3$ and —$N(R^2)S(O)_2R^3$;

$R^2$ and $R^3$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3).

Amide

The term "amide" as used herein includes reference to a compound comprising the basic structure shown as below:

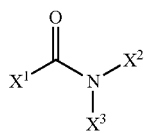

X¹ is selected from R¹, —OR¹, —C(O)R¹ and —C(O)OR¹;

X² and X³ are each independently selected from R¹, —C(O)R¹ and —C(O)OR¹;

R¹ is independently selected from hydrogen, halogen, trifluoromethyl, cyano, nitro, hydrocarbyl optionally substituted with 1, 2, 3, 4 or 5 R², —(CH$_2$)$_k$-heterocyclyl optionally substituted with 1, 2, 3, 4 or 5 R², —OR³, —C(O)R⁴, —C(O)N(R³)R⁴, —C(O)OR³, —OC(O)R³, —S(O)$_2$R³, —S(O)$_2$N(R³)R⁴, —N(R³)R⁴, —N(R³)N(R³)R⁴, —N(R³)C(O)R⁴ and —N(R³)S(O)$_2$R⁴;

R² is independently selected from halogen, trifluoromethyl, cyano, nitro, oxo, =NR³, —OR³, —C(O)R⁴, —C(O)N(R³)R⁴, —C(O)OR³, —OC(O)R⁴, —S(O)$_2$R³, —S(O)$_2$N(R³)R⁴, —N(R³)R⁴, —N(R³)N(R³)R⁴, —N(R³)C(O)R⁴ and —N(R³)S(O)$_2$R⁴;

R³ and R⁴ are each independently hydrogen or selected from hydrocarbyl and —(CH$_2$)$_k$-heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy; wherein k is an integer between 1 and 6 (e.g. 1, 2 or 3).

Amine

The term "amine" as used herein includes reference to a compound comprising the basic structure shown as below:

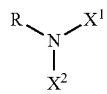

X¹ and X² are each independently selected from R¹, —C(O)R¹ and —C(O)OR¹;

R is independently selected from hydrocarbyl optionally substituted with 1, 2, 3, 4 or 5 R², —(CH$_2$)$_k$-heterocyclyl optionally substituted with 1, 2, 3, 4 or 5 R², —OR³, —C(O)R⁴, —C(O)N(R³)R⁴, —C(O)OR³, —OC(O)R³, —S(O)$_2$R³, —S(O)$_2$N(R³)R⁴, —N(R³)R⁴, —N(R³)N(R³)R⁴, —N(R³)C(O)R⁴ and —N(R³)S(O)$_2$R⁴;

R¹ is independently selected from hydrogen, halogen, trifluoromethyl, cyano, nitro, hydrocarbyl optionally substituted with 1, 2, 3, 4 or 5 R², —(CH$_2$)$_k$-heterocyclyl optionally substituted with 1, 2, 3, 4 or 5 R², —OR³, —C(O)R⁴, —C(O)N(R³)R⁴, —C(O)OR³, —OC(O)R³, —S(O)$_2$R³, —S(O)$_2$N(R³)R⁴, —N(R³)R⁴, —N(R³)N(R³)R⁴, —N(R³)C(O)R⁴ and —N(R³)S(O)$_2$R⁴;

R² is independently selected from halogen, trifluoromethyl, cyano, nitro, oxo, =NR³, —OR³, —C(O)R⁴, —C(O)N(R³)R⁴, —C(O)OR³, —OC(O)R⁴, —S(O)$_2$R³, —S(O)$_2$N(R³)R⁴, —N(R³)R⁴, —N(R³)N(R³)R⁴, —N(R³)C(O)R⁴ and —N(R³)S(O)$_2$R⁴;

R³ and R⁴ are each independently hydrogen or selected from hydrocarbyl and —(CH$_2$)$_k$-heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy; wherein k is an integer between 1 and 6 (e.g. 1, 2 or 3).

Peptide Bond

The term "peptide bond" as used herein includes reference to a covalent chemical bond formed between two amino acids when the carboxylic acid group of one molecule reacts with the amino group of the other molecule.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example C$_{1-6}$ alkyl or C$_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Independently

Where two or more moieties are described as being "each independently" selected from a list of atoms or groups, this means that the moieties may be the same or different. The identity of each moiety is therefore independent of the identities of the one or more other moieties.

Embodiments of the invention are described below. Preferred features of each aspect of the invention are as for each of the other aspects mutatis mutandis. Moreover, it will be appreciated that the features specified in each embodiment may be combined with other specified features, to provide further embodiments.

The invention involves the use of cycloheptapeptide and cyclohepta-depsipeptide compounds including derivatives of 1, 2 or 3. Preferably the compounds are cycloheptapeptide and cyclohepta-depsipeptide compounds of which at least one of the peptide bonds is resulted from the coupling of the carbolic acid group of an amino acid and the amino group of an α-amino-cyclic-acetic acid. Further preferred are cycloheptapeptide and cyclohepta-depsipeptide compounds of which the nitrogen atom of at least one of the peptide bonds may be alkylated.

In one embodiment, the invention provides compounds of the formulae (I) and (II):

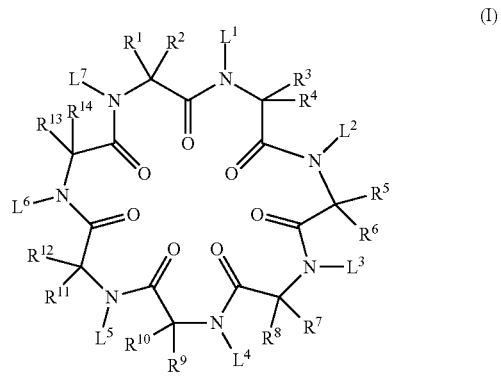

(I)

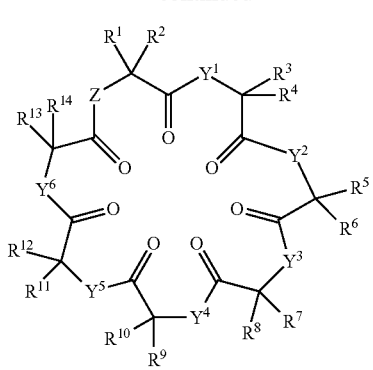

(II)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently hydrogen, halogen or a moiety comprising 1 to 30 plural valence atoms selected from carbon, nitrogen, oxygen and sulphur;

At least one of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a cyclic group;

$R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ may be taken together with the carbon atoms to which they are attached to form one or more carboxyl groups (C=O); or while one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is hydrogen, halogen, hydrocarbyl or alkoxy, the other one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is independently selected from $R^{15}$, —$OR^{15}$, —$C(O)R^{15}$ and —$C(O)OR^{15}$;

$R^{15}$ is independently selected from hydrogen, halogen, trifluoromethyl, cyano, nitro, hydrocarbyl optionally substituted with 1, 2, 3, 4 or 5 $R^{16}$, —$(CH_2)_k$-heterocyclyl optionally substituted with 1, 2, 3, 4 or 5 $R^{16}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$;

$R^{16}$ is independently selected from halogen, trifluoromethyl, cyano, nitro, oxo, =$NR^{17}$, —$OR^{17}$, —$C(O)R^{18}$, —$C(O)N(R^{17})R^{18}$, —$C(O)OR^{17}$, —$OC(O)R^{18}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$;

$R^{17}$ and $R^{18}$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3);

$L^1$, $L^2$, $L^3$, $L^4$, $L^5$, $L^6$ and $L^7$ are each independently selected from $R^{15}$, —$C(O)R^{15}$ and —$C(O)OR^{15}$;

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $L^1$, $L^2$, $L^3$, $L^4$, $L^5$, $L^6$ and $L^7$ may be taken together with the carbon atoms and the nitrogen atoms to which they are attached to form one or more cyclic groups which is optionally substituted with halogen or a moiety comprising 1 to 30 plural valence atoms selected from carbon, nitrogen, oxygen and sulphur;

Z is selected from oxygen, nitrogen, hydrocarbyl, or alkoxy;

$Y^1$, $Y^2$, $Y^3$, $Y^4$, $Y^5$ and $Y^6$ are each independently selected from oxygen, sulfur, nitrogen with substitution of an $L_1$, $L_2$, $L_3$, $L_4$, $L_5$ or $L_6$ group, $C_{1-6}$ alkyl or $C_{1-6}$ alkoxy. At least one of $Y^1$, $Y^2$, $Y^3$, $Y^4$, $Y^5$ and $Y^6$ is nitrogen with substitution of an $L_1$, $L_2$, $L_3$, $L_4$, $L_5$ or $L_6$ group when Z is oxygen, hydrocarbyl or alkoxy or an enantiomer thereof or a pharmaceutically acceptable salt or pro-drug thereof.

Examples of compounds of the invention include those shown below. It will of course be appreciated that, where appropriate, each compound may be in the form of the free compound, an enantiomer, an acid or base addition salt, or a prodrug.

EXAMPLE

The dry stem barks (3.0 kg) from the decaying wood of *Maytenus variabilis* (Loes.) C. Y. Cheng (Celastraceae) were collected through purchase from Guizhou, China. A primary screening showed that the methanol extract made from a small of amount of the plant materials (5 g) exhibited complete inhibition activity against HCT116 cancer cells at a concentration of 0.625 μg/mL. All the collected barks were thus submitted to phytochemical study in order to identify anticancer compounds. As a result, three novel cyclic peptides (1, 2 and 3) were isolated from the methanol extract of this plant.

The cyclopeptides 1 and 2 demonstrated potent activity against a panel of cancer cell lines including oral epidermoid (KB), colon (HCT116), prostate (LNCaP), breast (MCF-7) and lung (A549) carcinoma cell lines (Tables 2 and 3). Compound 1 displayed more potent cell killing activity than those of paclitaxel and vinblastine. It also showed comparative activity to the anticancer compound maytansine. Furthermore, compound 1 were able to inhibit cancer cells by more than 90% at much lower concentration than those of maytansine, paclitaxel and vinblastine (Table 4).

Different from the common cyclopeptides, which are normally formed from the common amino acids listed in Table 1, the structures of 1, 2 and 3 contain peptide bond(s) made from a novel amino acid. The novel amino acid was identified as α-amino-2,3-dimethyl-cyclopropaneacetic acid (DMCPA), which has not been reported in the literature. We believe that the novel amino acid forms key substructural component(s) responsible for the cancer cell killing activity of the isolated cyclopeptides.

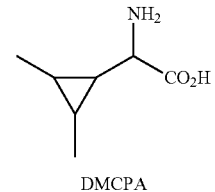

DMCPA

When one of the DMCPA residues is replaced by a leucine residue, the cancer cell killing activity significantly reduced. In comparison with 1, 3 contains only one DMCPA residue, which resulted in reduction of at least 100 times in activity for 3.

In the literature, we found a cycloheptapeptide (ternatin), which is structurally similar to 1, 2 and 3, but the compound does not have a DMCPA residue. Ternatin was reported to possess cytotoxic activity against murine P388 leukemia cells with $IC_{50}$ value of 1.63 μM (Feng Y J, Blunt J W, Cole A L J, Cannon J F, Robinson W T, Munro M H G. Journal of Organic Chemistry 2003; 68: 2002-2005.). To compare with the literature data of ternatin, we evaluated the effects of 1 and 2 on murine P388 leukemia cells, which showed that 1 and 2 were able to inhibit cell growth of murine P388 leukemia cells by 100% at a concentration of 10 ng/mL. The result demonstrated that the cyclopeptides having the DMCPA residue (i.e. 1 and 2) possess much more potent biologically activity than ternatin.

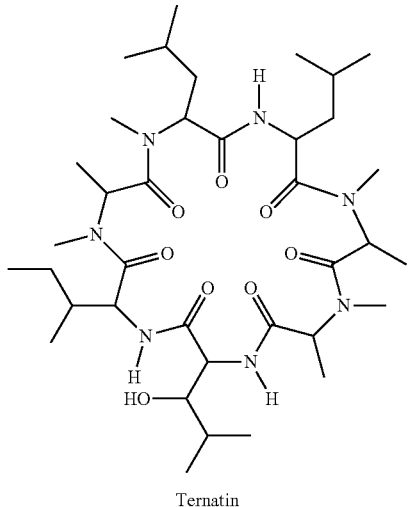 [SMILES: CCC(C)C1NC(=O)C(C(O)C(C)C)NC(=O)C(C)N(C)C(=O)C(C)N(C)C(=O)C(CC(C)C)NC(=O)C(CC(C)C)N(C)C(=O)C(C)N(C)C1=O]

Ternatin

Further, the activity is affected by the presence of an adjacent functional group that may have interference with the DMCPA residue. For example, although compound 2 has comparative activity to paclitaxel, it showed much lower activity than 1. The only structural difference between the two compounds is that the leucine residue near the DMCPA residue in 1 is substituted by a hydroxy group in 2. This hydroxy substitute might have greatly disrupted the binding interaction between the DMCPA residue and the DMCPA targeted protein.

Ternatin has been reported to be a potent inhibitor of fat accumulation against 3T3-L1 murine adipocytes (Shimokawa K, Mashima I, Asai A, Yamada K, Kita M, Uemura D. Tetrahedron Letters 2006; 47: 4445-4448.). Since the chemical structures of 1, 2 and 3 are structurally similar to that of ternatin, we believe that the three compounds may also have inhibition activity against 3T3-L1 murine adipocytes. We further believe that 1, 2 and 3 may exhibit even much higher fat-accumulation inhibitory effects than that of ternatin because these compounds contain DMCPA residue(s). In an animal study, we demonstrated that the body weights of mice were significantly decreased after drug treatment of 1. The average weight of mice (10 mice) dropped 1.5 g and 2.2 g after the first treatment (i.e. injection) with 1 at a dose of 1 mg/kg and 2 mg/kg, respectively, but the weight of the mice kept relatively stable after the first treatment. After six treatments (twice a week), the average weight of mice dropped 1.7 g and 4.7 g at 1 mg/kg and 2 mg/kg, respectively. No mice died during the six treatments, and the weight of mice gained back after the treatment stopped, which showed that the effects of compound 1 on the mice are reversible. No sign of toxicity was observed from dissection of the mice.

TABLE 2

Cytotoxic activity ($IC_{50}$ values) of 1, 2 and 3

| Compound | Bioactivity: $IC_{50}$ (nM) | | | | |
|---|---|---|---|---|---|
| | KB | HCT116 | LNCaP | A549 | MCF7 |
| 1 | 0.05 | 0.25 | 0.42 | 0.24 | 0.26 |
| 2 | 0.79 | 2.62 | Not tested | 6.35 | 5.83 |
| 3 | 12.5 | 43.5 | Not tested | 51.8 | 26.6 |
| Maytansine | 0.16 | Not tested | 0.56 | 3.18 | 0.69 |
| Paclitaxel | 3.38 | 5.78 | 15.9 | 4.81 | 3.24 |

TABLE 3

Cytotoxic activity ($IC_{90}$ values) of 1, 2 and 3

| Compound | Bioactivity: $IC_{90}$ (nM) | | | |
|---|---|---|---|---|
| | KB | HCT116 | A549 | MCF7 |
| 1 | 1.65 | 0.69 | 1.02 | 1.47 |
| 2 | 11.4 | Not tested | 6.84 | 9.21 |
| 3 | Not tested | Not tested | Not tested | Not tested |
| Maytansine | ~5 | Not tested | >40 | >20 |
| Paclitaxel | >20 | >20 | >20 | >30 |
| Vinblastine | 10.1 | Not tested | >40 | >50 |

It is also shown that Compounds 1, 2 and 3 as embodied in this invention are able to inhibit fat-accumulation in mice.

Accordingly, it is envisaged that the embodied compounds can be used in the treatment, prevention or delay of progression of cancer or obesity in a human patient. It is also envisaged that a composition including a pharmaceutical composition or a plant extract having the embodied compounds can be used in the treatment, prevention or delay of progression of cancer or obesity in a human patient. It is further envisaged that the composition can be an extract or a separated fraction from any natural sources, for example, any plant materials, and microorganisms.

Methodology and Characterization

Plant Materials.

The dry stem barks (3.0 kg) from the decaying wood of *Maytenus variabilis* (Loes.) C. Y. Cheng (Celastraceae) were collected from Guizhou Province, China.

Extraction and Isolation.

The dried and milled stem barks (3 kg) of *Maytenus variabilis* were extracted with methanol (MeOH) to afford an extract, which was subsequently defatted with n-hexane and partitioned with $CHCl_3$. Separation of the $CHCl_3$-soluble fraction by column chromatography on Si gel and RP-18 Si gel columns led to the isolation of 1, 2 and 3.

Figure 1B:
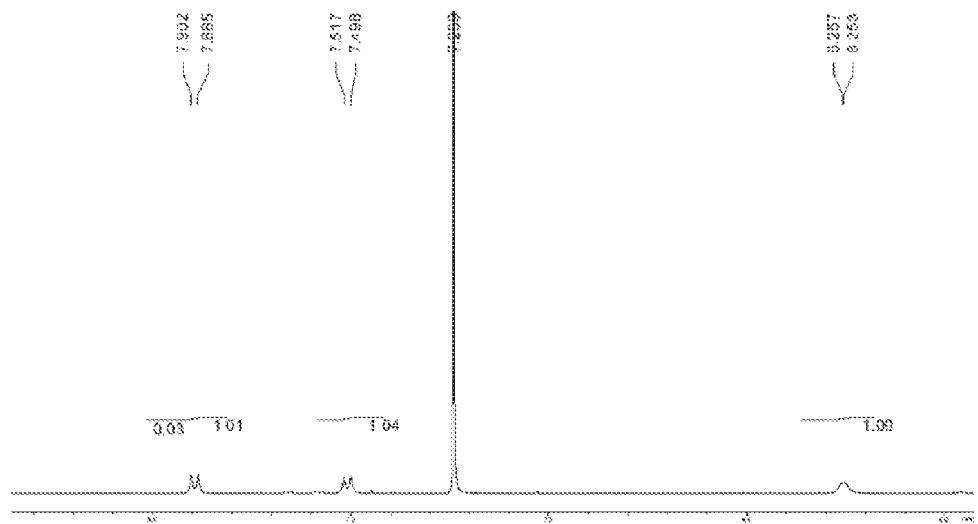
FIG. 1(B) shows $^1$H NMR data of 1 (CDCl$_3$).
Figure 1C:
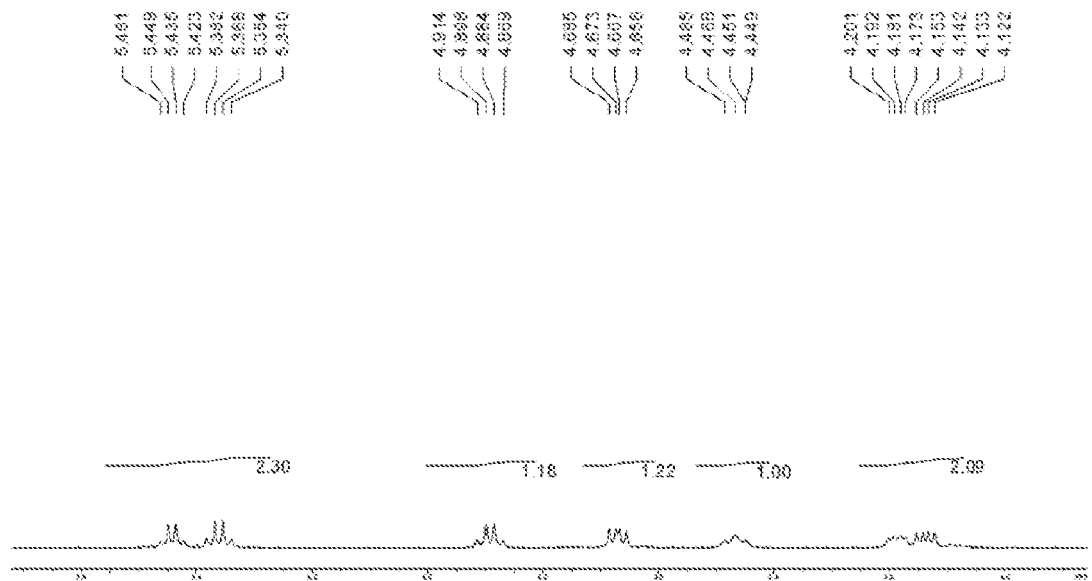
FIG. 1(C) shows $^1$H NMR data of 1 (CDCl$_3$).
Figure 1D:
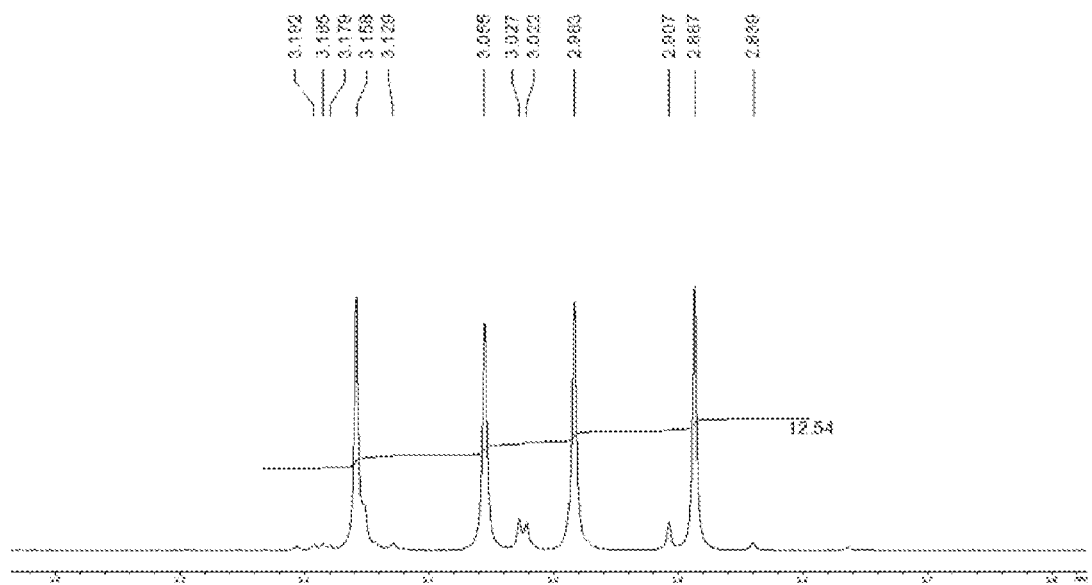
FIG. 1(D) shows $^1$H NMR data of 1 (CDCl$_3$).
Figure 1E:
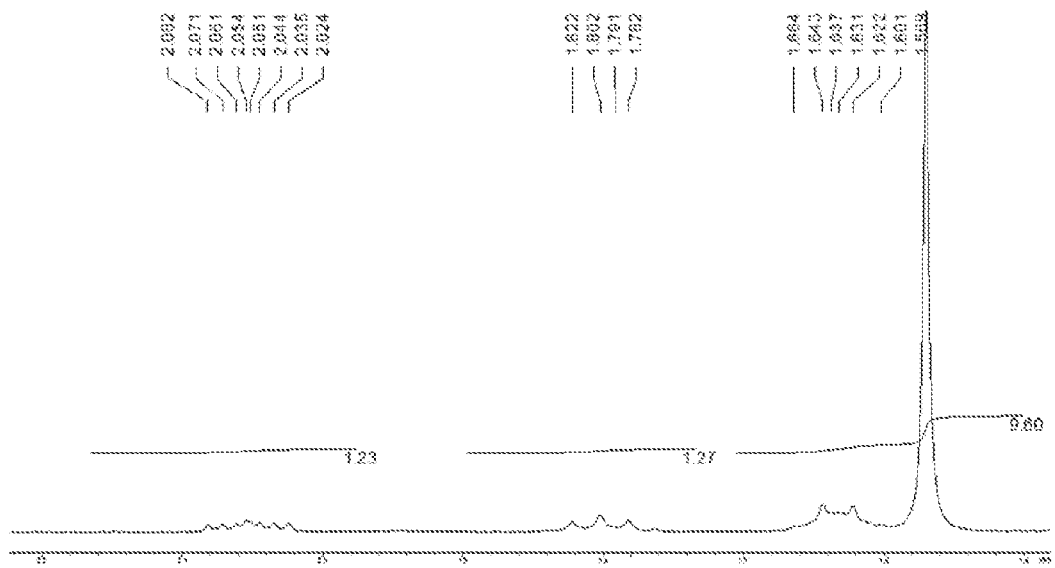
FIG. 1(E) shows $^1$H NMR data of 1 (CDCl$_3$).
Figure 1F:
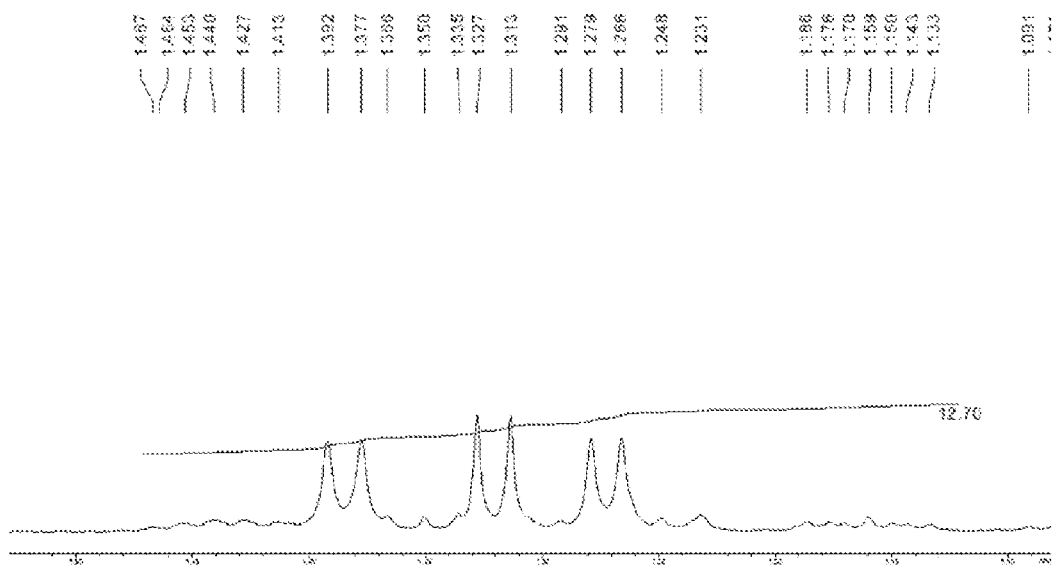
FIG. 1(F) shows $^1$H NMR data of 1 (CDCl$_3$).
Figure 1G:
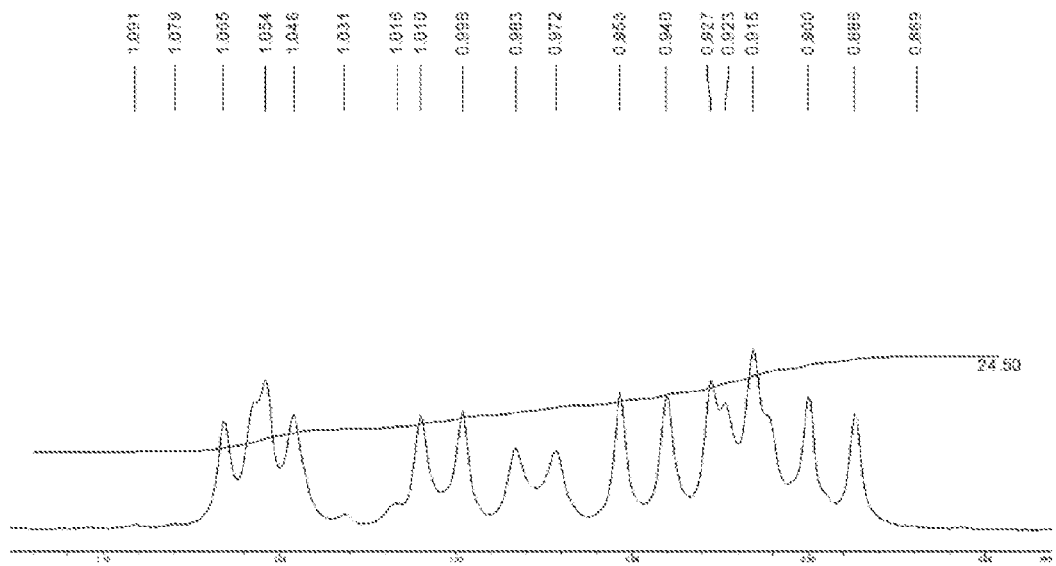
FIG. 1(G) shows $^1$H NMR data of 1 (CDCl$_3$).
Figure 1H:
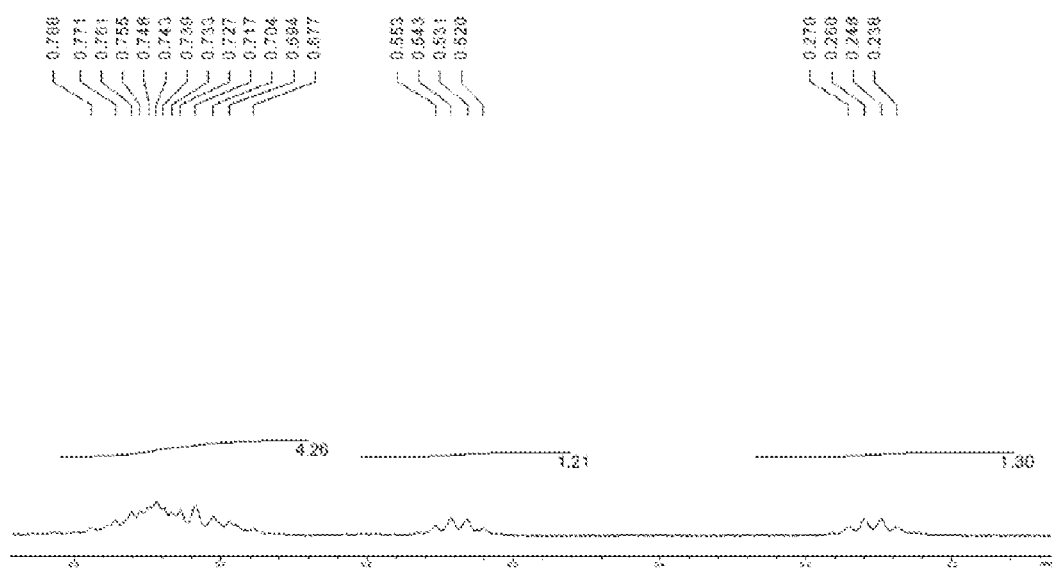
FIG. 1(H) shows $^1$H NMR data of 1 (CDCl$_3$).
Figure 2A:
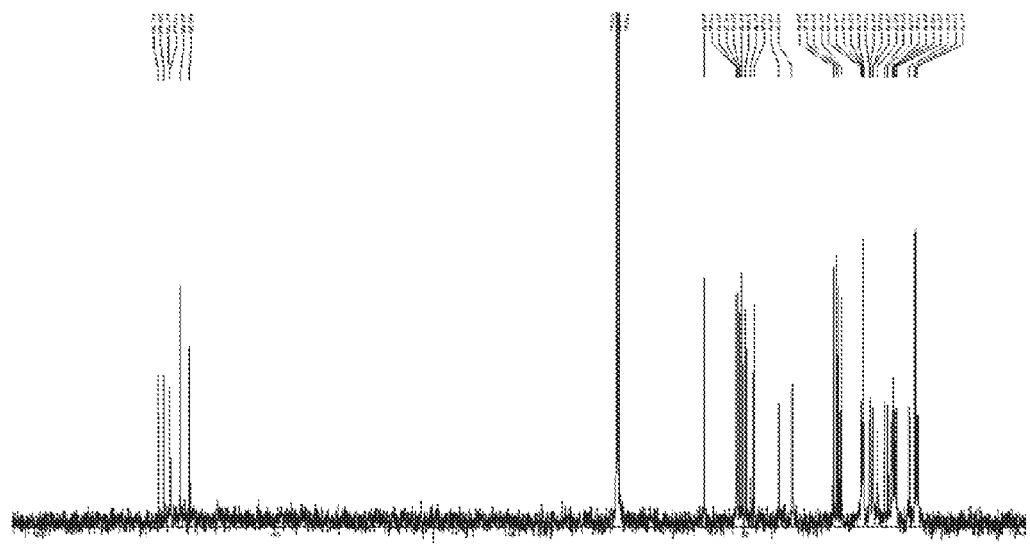
FIG. 2(A) shows $^{13}$C NMR data of 1 (CDCl$_3$).
Figure 2B:
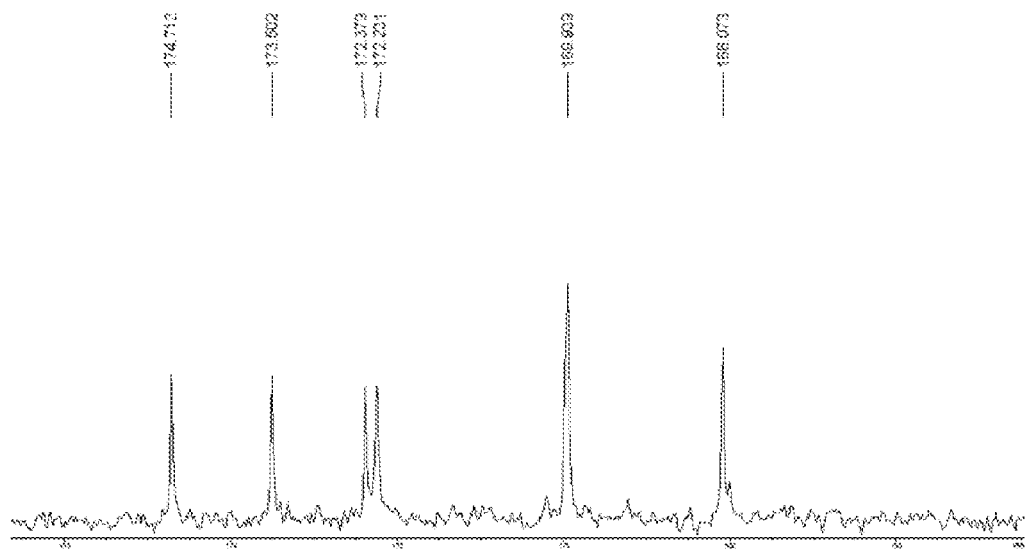
FIG. 2(B) shows $^{13}$C NMR data of 1 (CDCl$_3$).
Figure 2C:
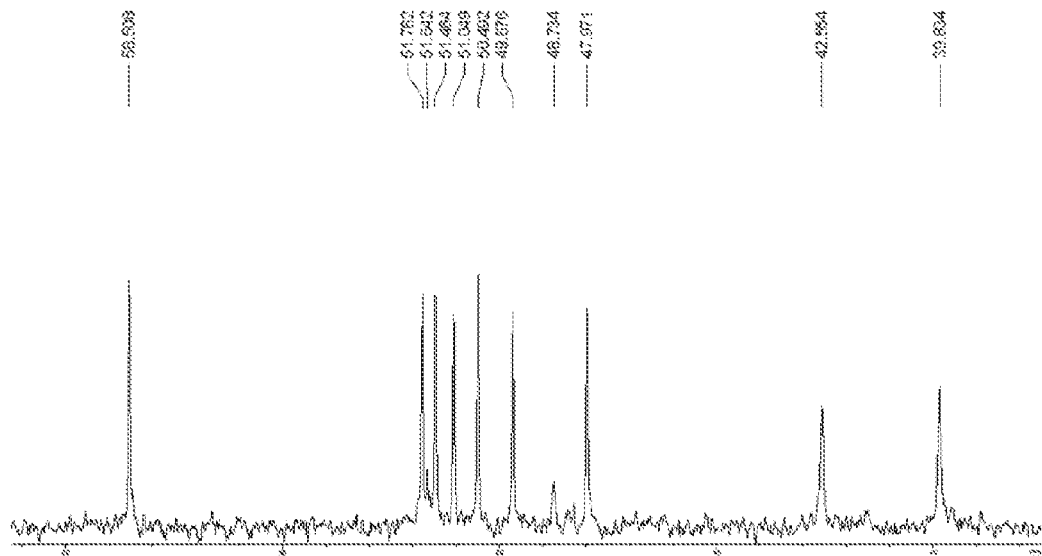
FIG. 2(C) shows $^{13}$C NMR data of 1 (CDCl$_3$).
Figure 2D:
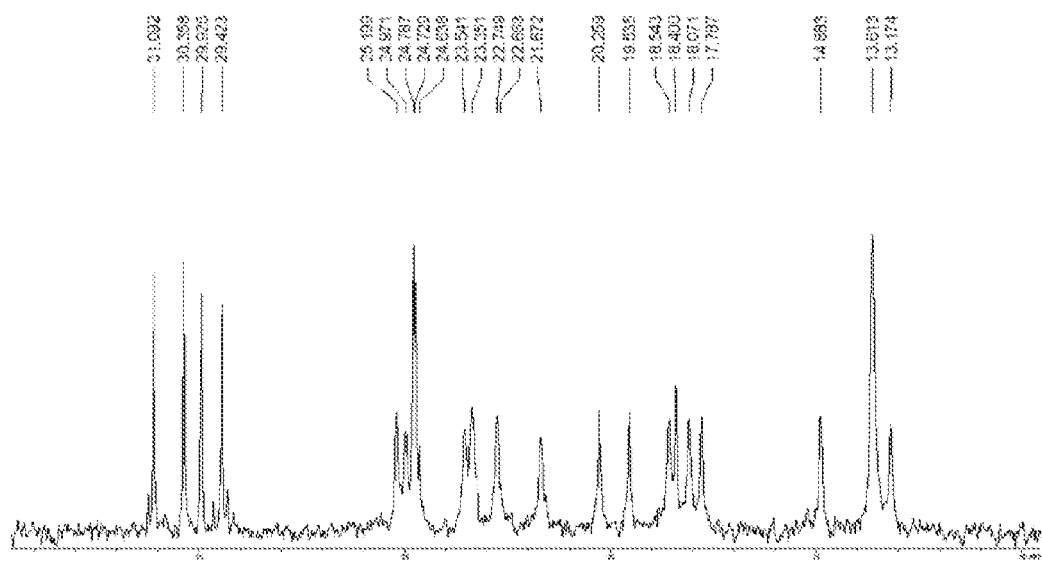
FIG. 2(D) shows $^{13}$C NMR data of 1 (CDCl$_3$).

Compound 1, $[\alpha]_D^{20}$ −2.9° (c 0.17, MeOH); was obtained as a white powder with a molecular formula of $C_{39}H_{67}N_7O_7$ by positive HRESIMS ([M+H]$^+$ m/z 746.5123, calcd. 746.5175) and NMR studies (Tables 4 and 5, and FIGS. 1(A)-1(H) and FIGS. 2(A)-2(D)). In combination of analysis of 2D NMR data including $^1H$—$^1H$ COSY, HMQC, HMBC, TOCSY and ROESY spectral data, the structure of compound 1 was determined as shown.

Figure 3A:
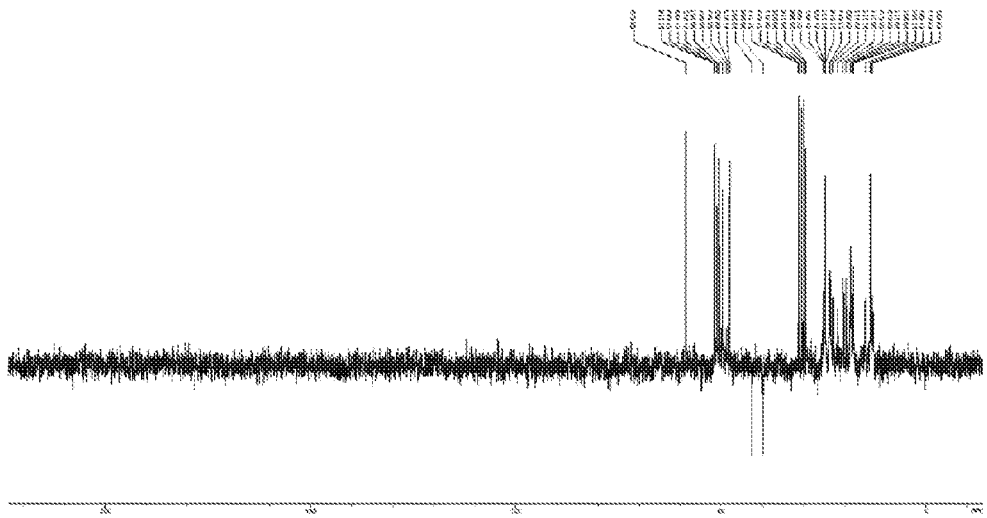
FIG. 3(A) shows DEPT-135 NMR data of 1 (CDCl$_3$).
Figure 3B:
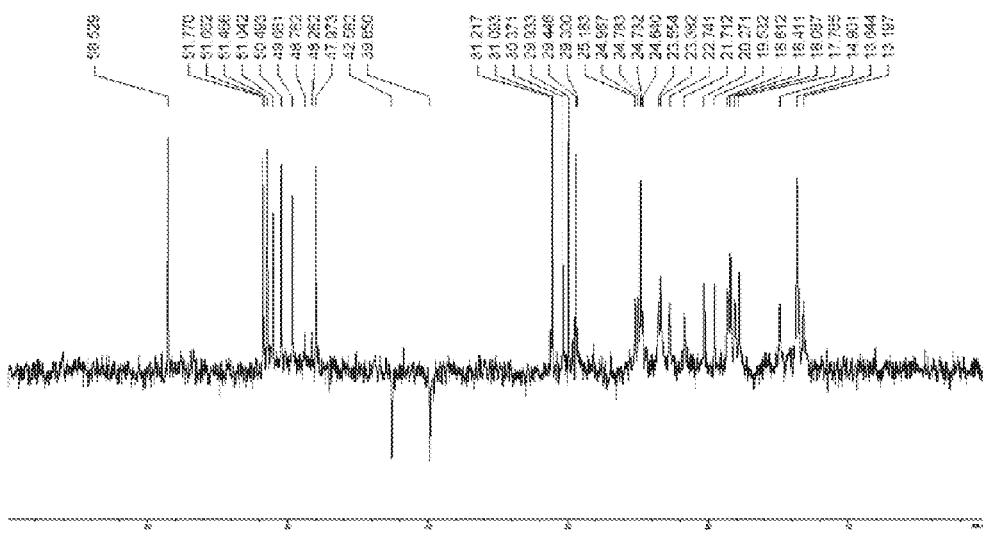
FIG. 3(B) shows DEPT-135 NMR data of 1 (CDCl$_3$).
Figure 4A:
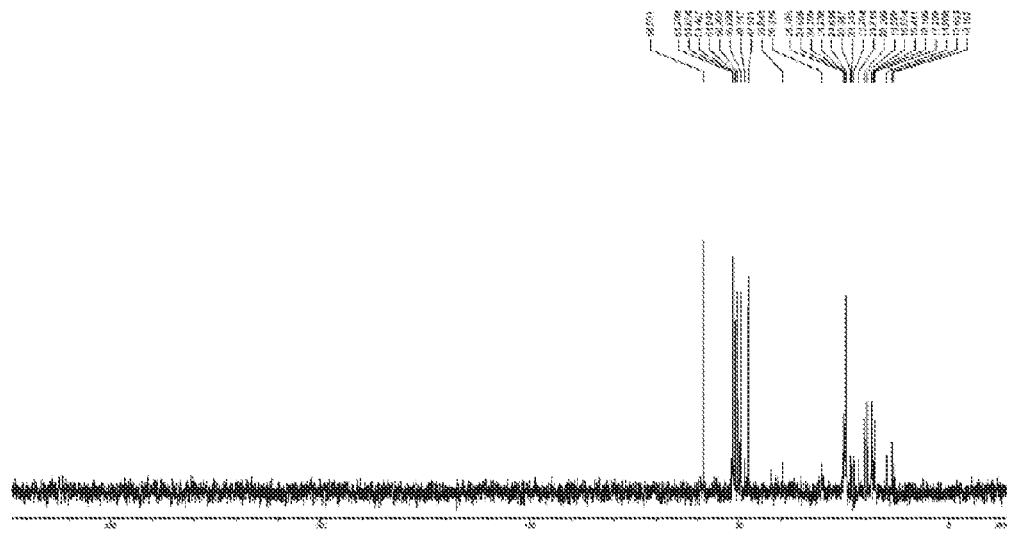
FIG. 4(A) shows DEPT-90 NMR data of 1 (CDCl$_3$).
Figure 4B:
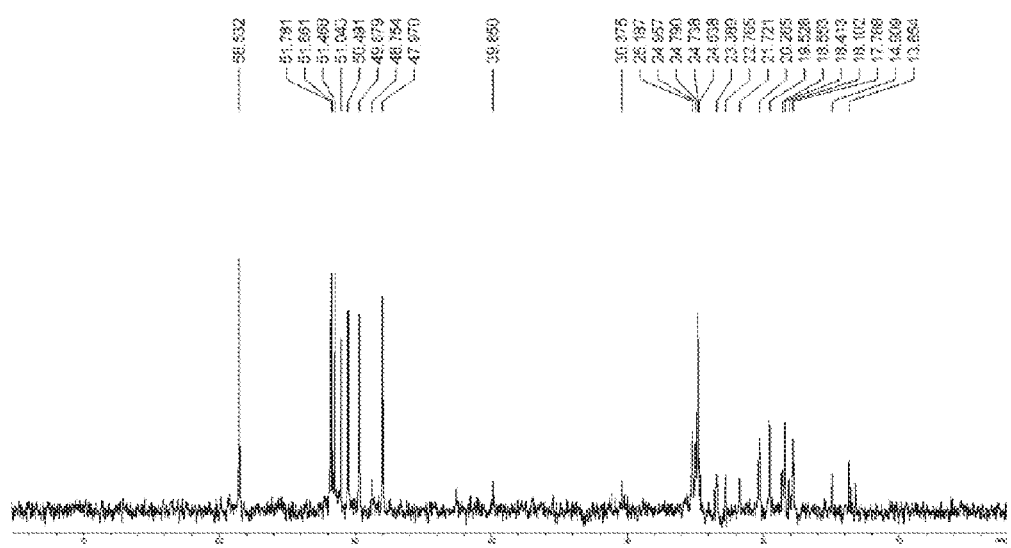
FIG. 4(B) shows DEPT-90 NMR data of 1.

Compound 2, $[\alpha]_D^{20}$ −3.5° (c 0.23, MeOH); was obtained as a white powder with a molecular formula of $C_{39}H_{68}N_7O_8$ by positive HRESIMS ([M+H]$^+$ m/z 762.5077, calcd. 762.5124) and NMR studies (Tables 4 and 5, and FIGS. 3(A)-3(B) and FIGS. 4(A)-4(B)). In combination of analysis 2D NMR data including $^1$H—$^1$H COSY, HMQC, HMBC, TOCSY and ROESY spectral data, the structure of compound 2 was determined as shown.

Figure 5A:
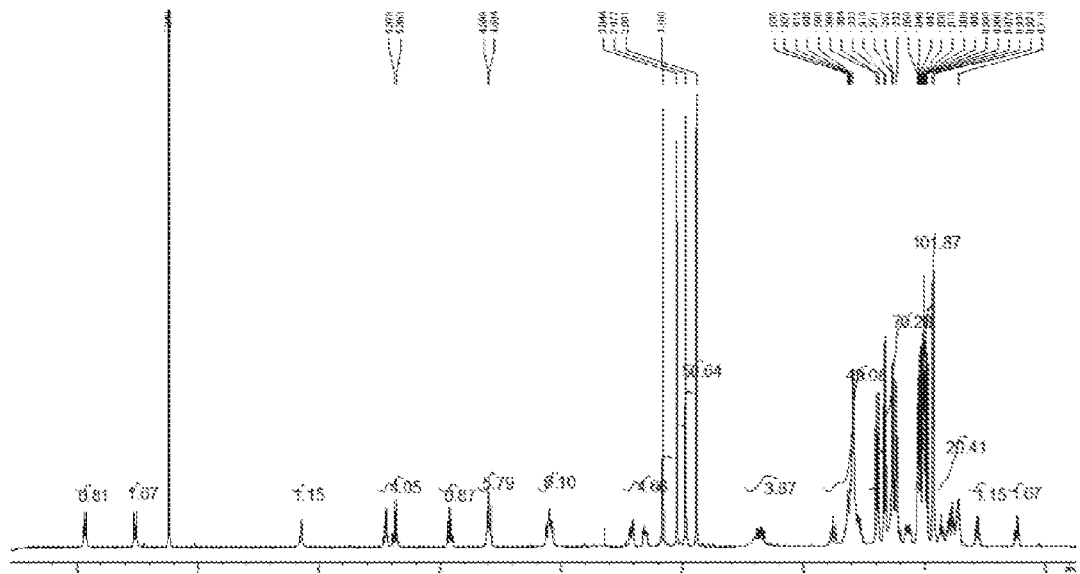
FIG. 5(A) shows $^1$H NMR data of 2 (CDCl$_3$).
Figure 5B:
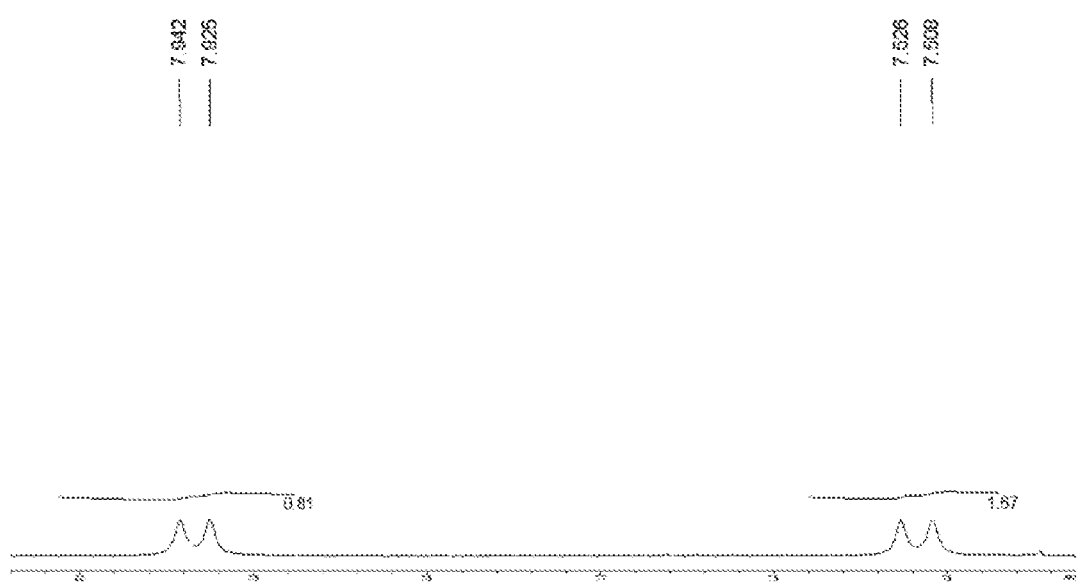
FIG. 5(B) shows $^1$H NMR data of 2 (CDCl$_3$).
Figure 5C:
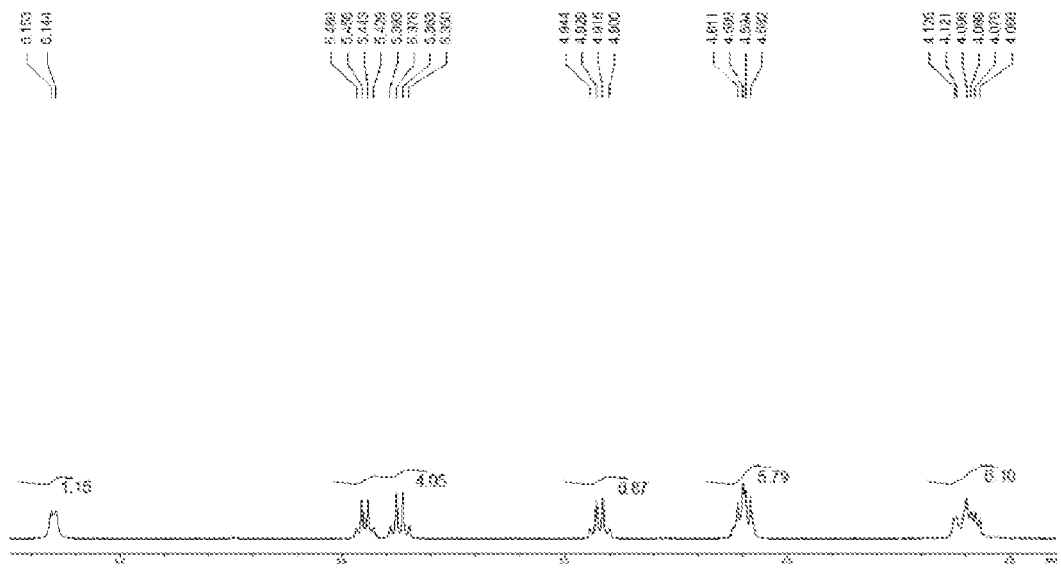
FIG. 5(C) shows $^1$H NMR data of 2 (CDCl$_3$).
Figure 5D:
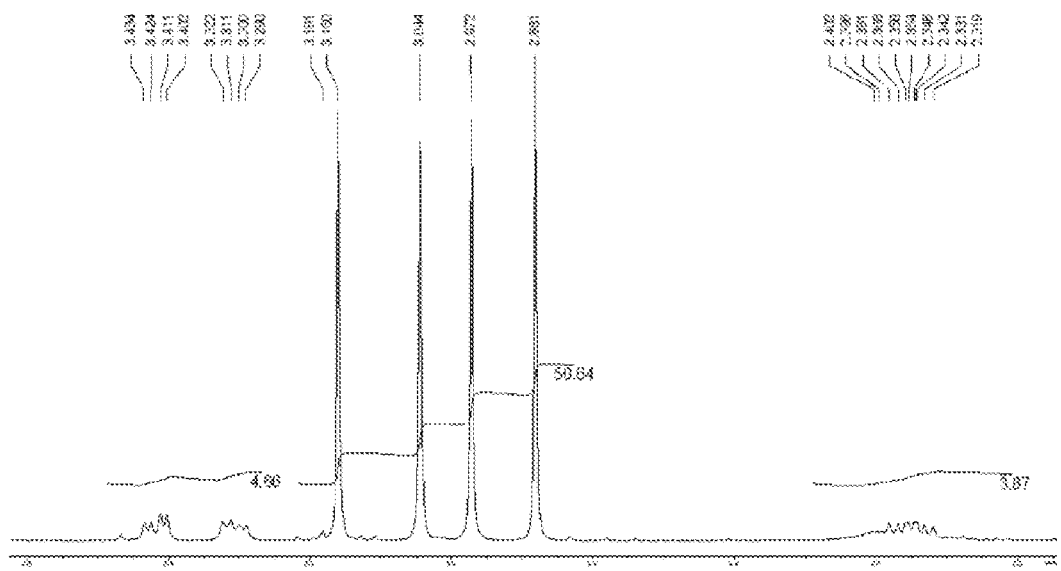
FIG. 5(D) shows $^1$H NMR data of 2 (CDCl$_3$).
Figure 5E:
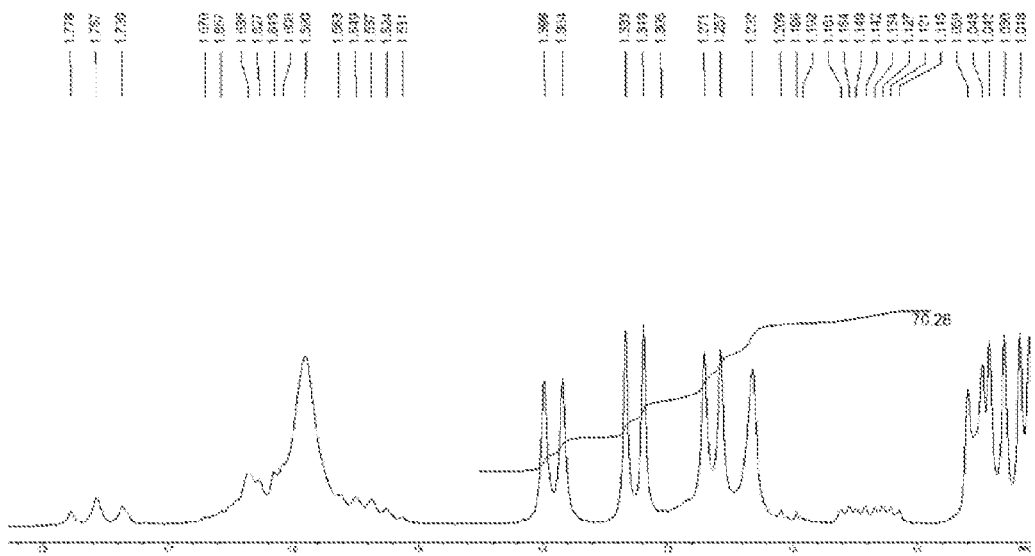
FIG. 5(E) shows $^1$H NMR data of 2 (CDCl$_3$).
Figure 5F:
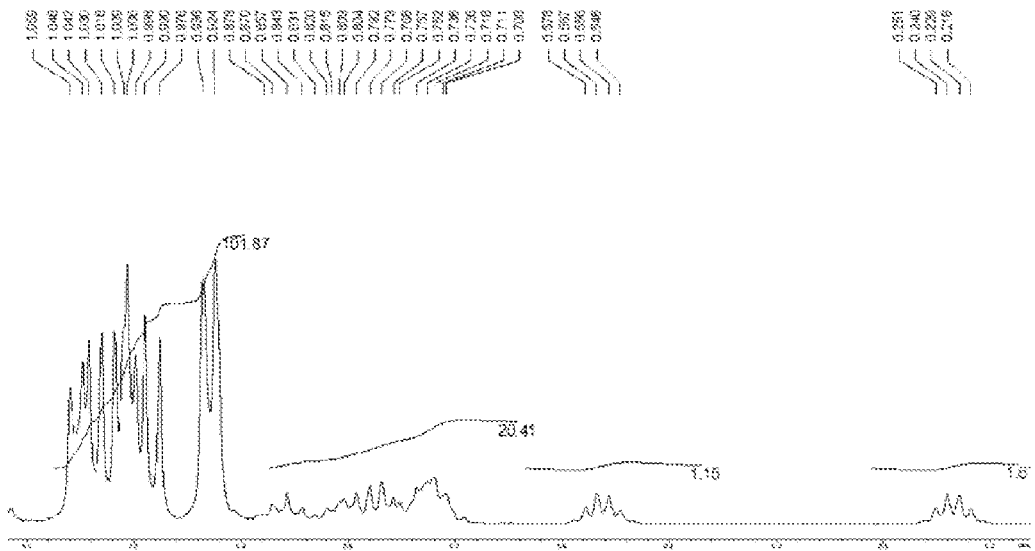
FIG. 5(F) shows $^1$H NMR data of 2 (CDCl$_3$).
Figure 6A:
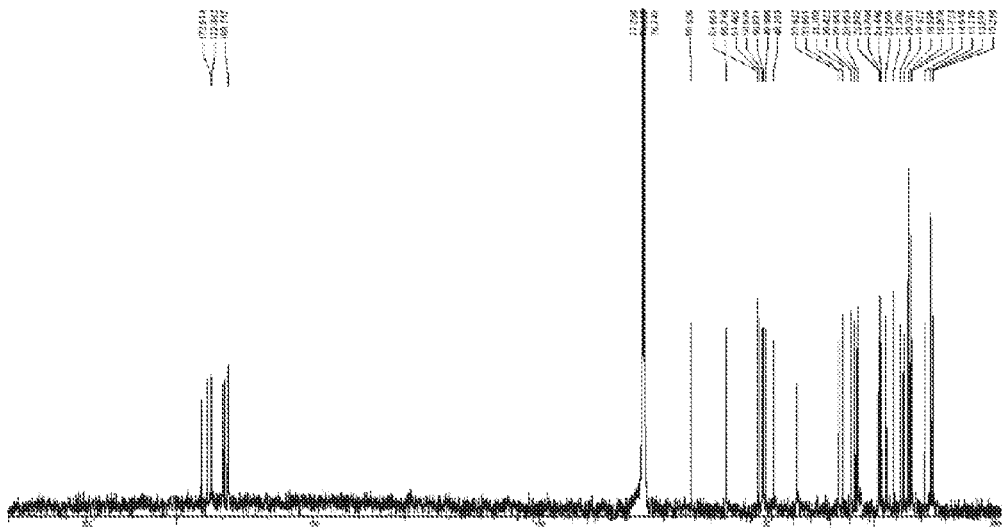
FIG. 6(A) shows $^{13}$C NMR data of 2 (CDCl$_3$).
Figure 6B:
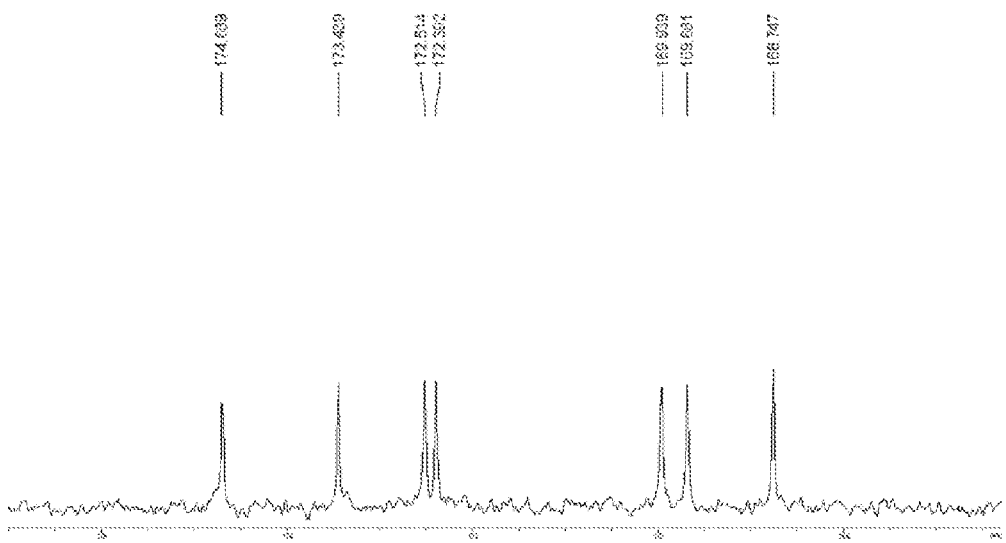
FIG. 6(B) shows $^{13}$C NMR data of 2 (CDCl$_3$).
Figure 6C:
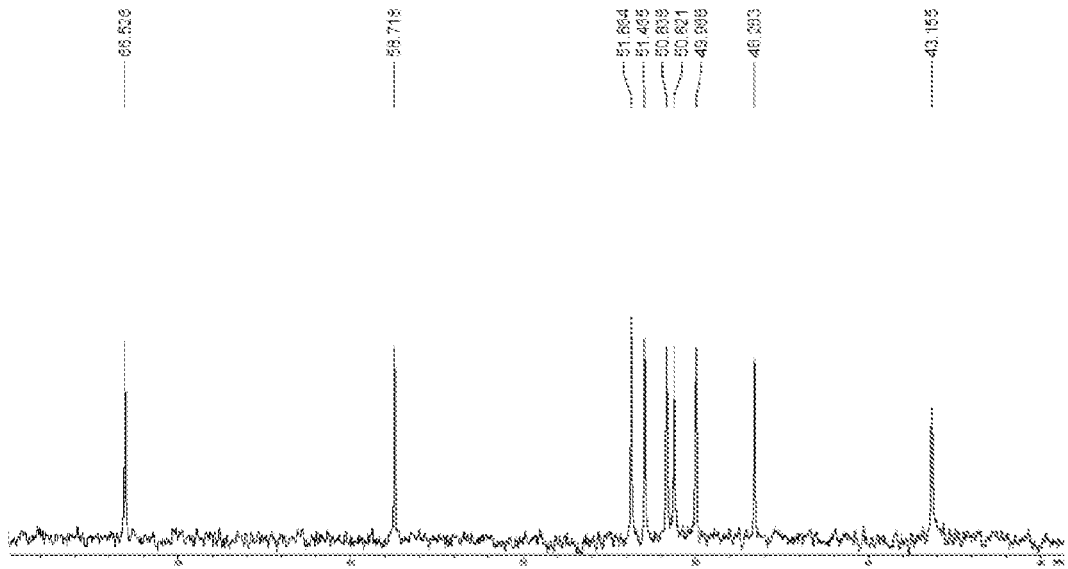
FIG. 6(C) shows $^{13}$C NMR data of 2 (CDCl$_3$).
Figure 6D:
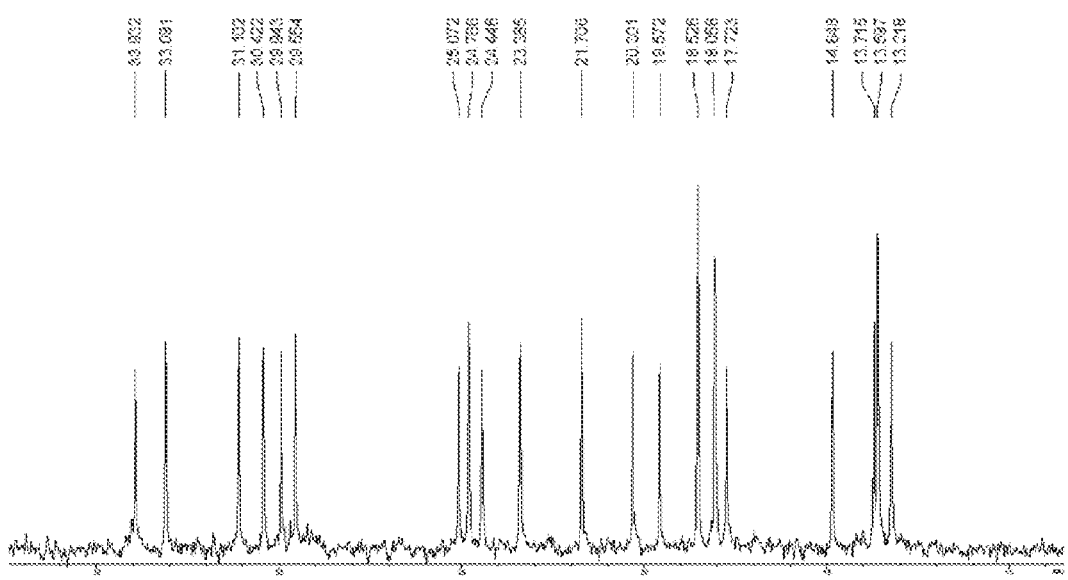
FIG. 6(D) shows $^{13}$C NMR data of 2 (CDCl$_3$).
Figure 7A:
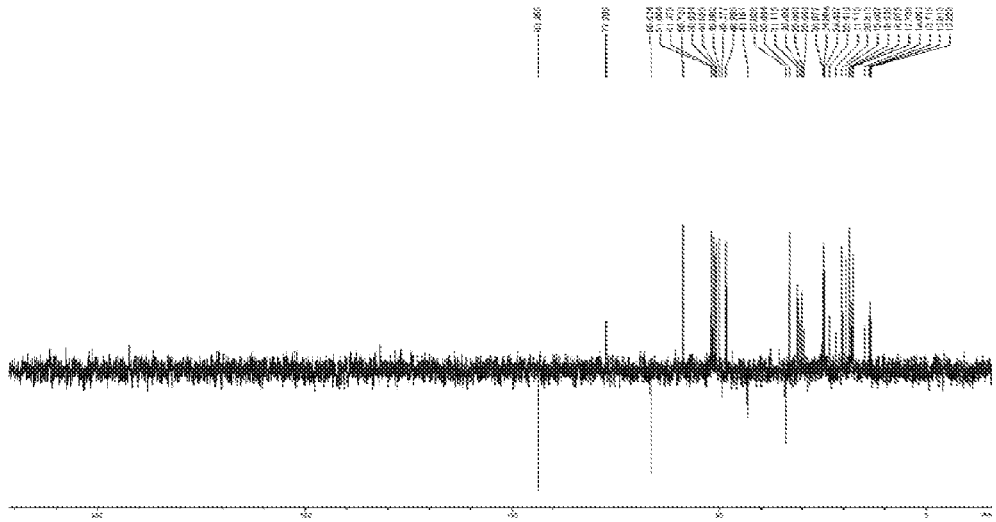
FIG. 7(A) shows DEPT-135 NMR data of 2 (CDCl$_3$).
Figure 7B:
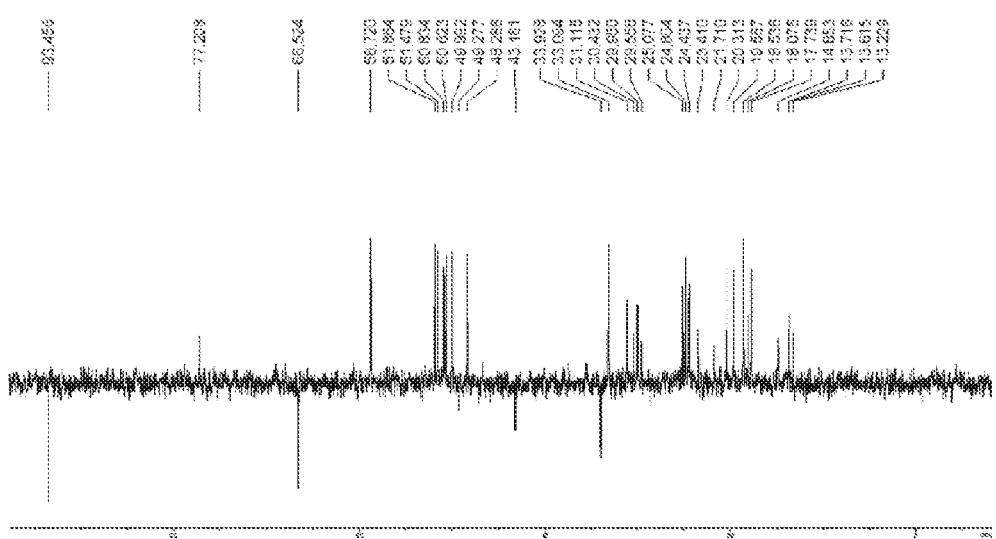
FIG. 7(B) shows DEPT-135 NMR data of 2 (CDCl$_3$).
Figure 8A:
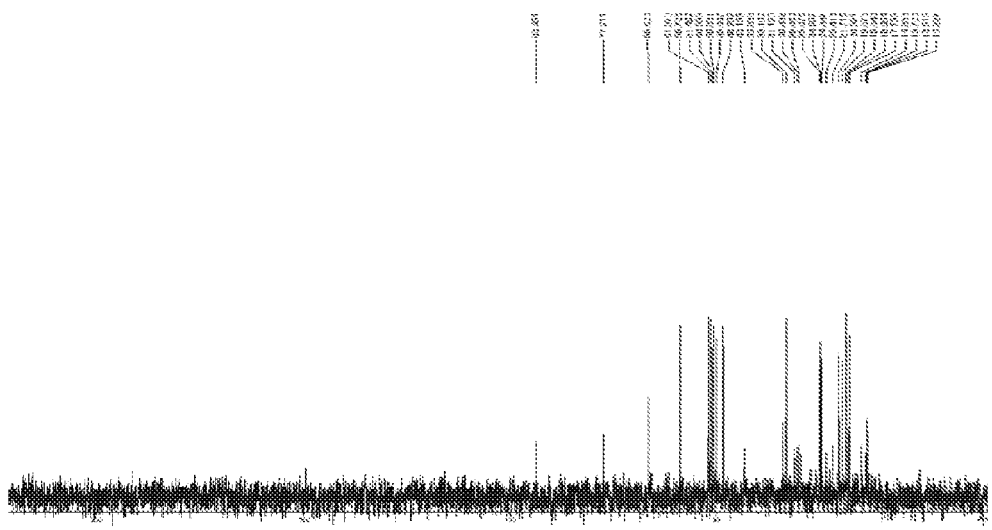
FIG. 8(A) shows DEPT-90 NMR data of 2 (CDCl$_3$).
Figure 8B:
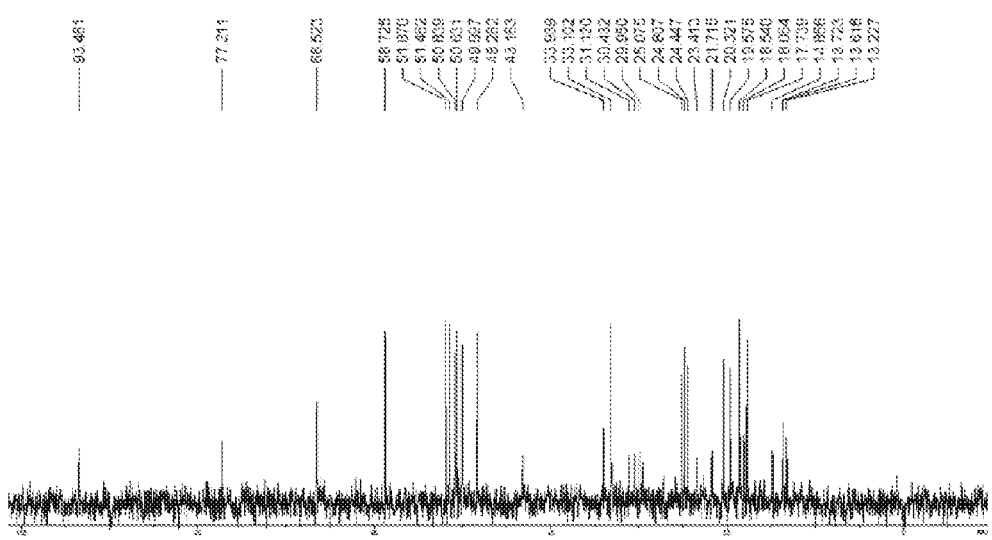
FIG. 8(B) shows DEPT-90 NMR data of 2.
Figure 9A:
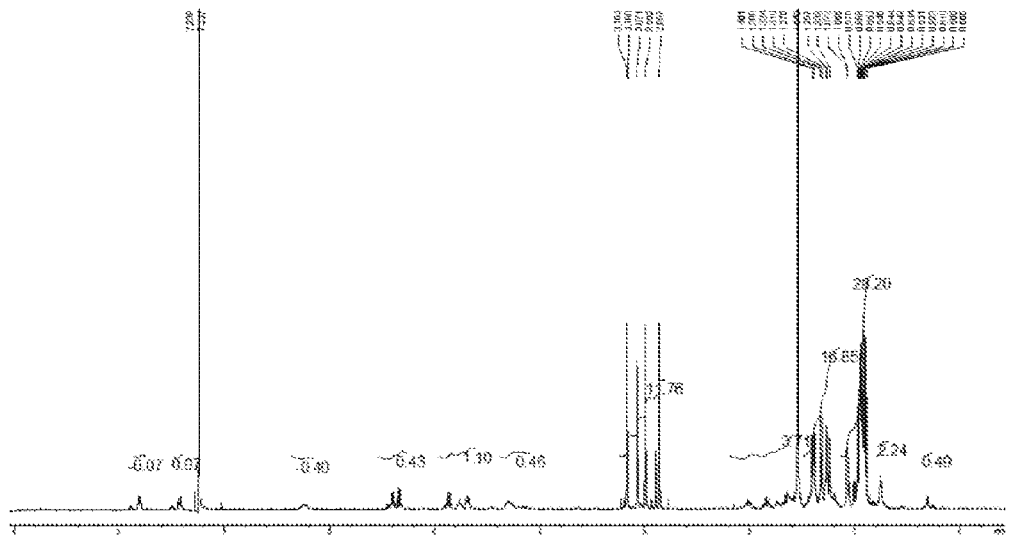
FIG. 9(A) shows $^1$H NMR data of 3 (CDCl$_3$).
Figure 9B:
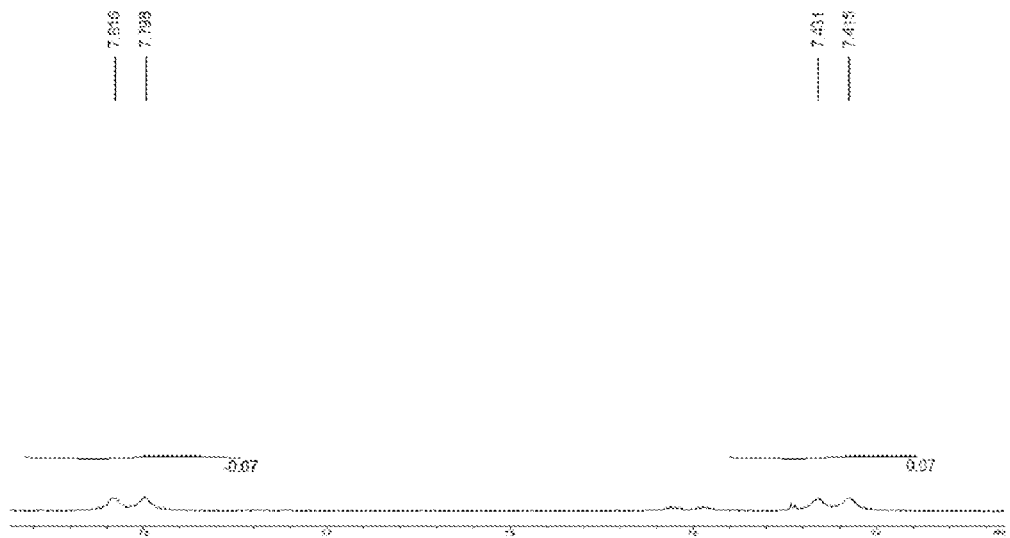
FIG. 9(B) shows $^1$H NMR data of 3 (CDCl$_3$).
Figure 9C:
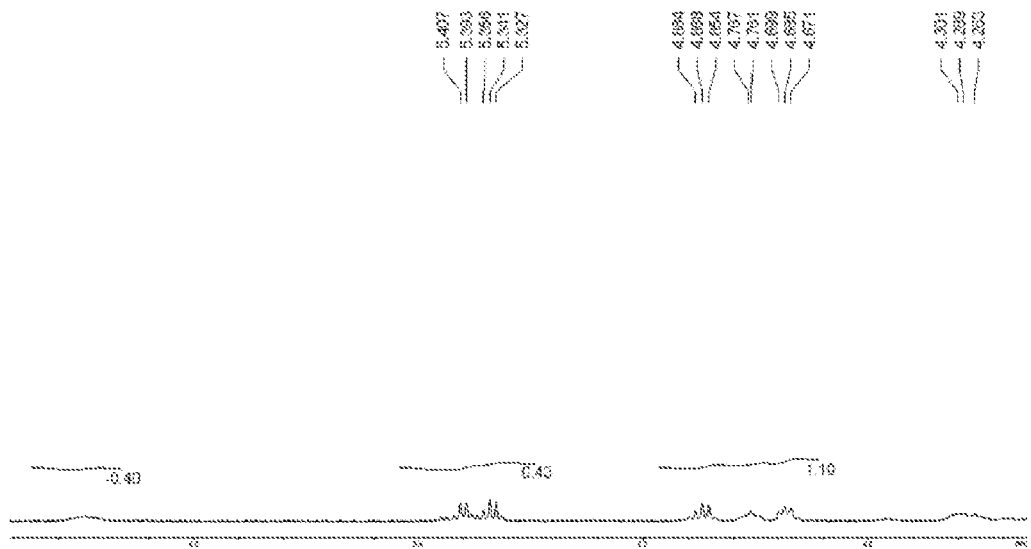
FIG. 9(C) shows $^1$H NMR data of 3 (CDCl$_3$).
Figure 9D:
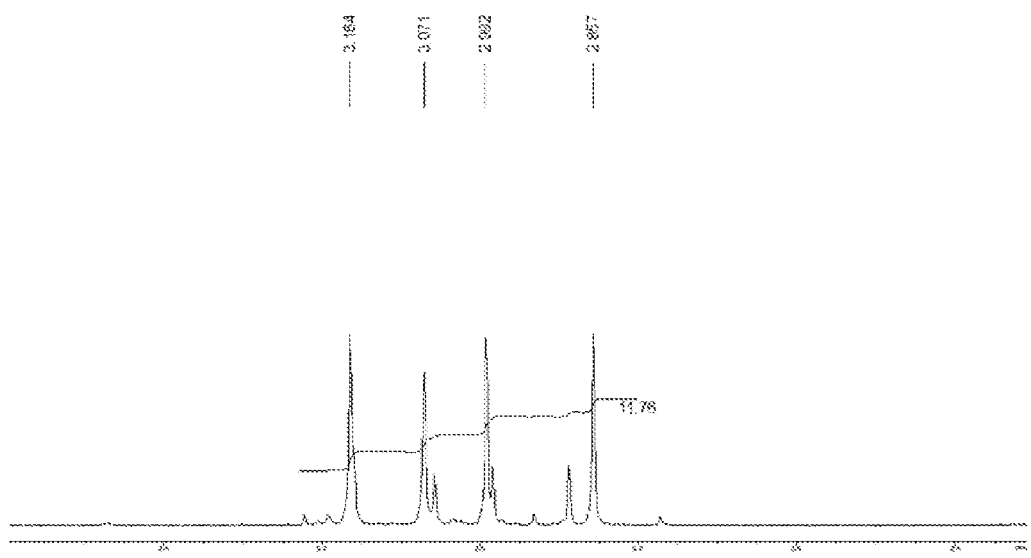
FIG. 9(D) shows $^1$H NMR data of 3 (CDCl$_3$).
Figure 9E:
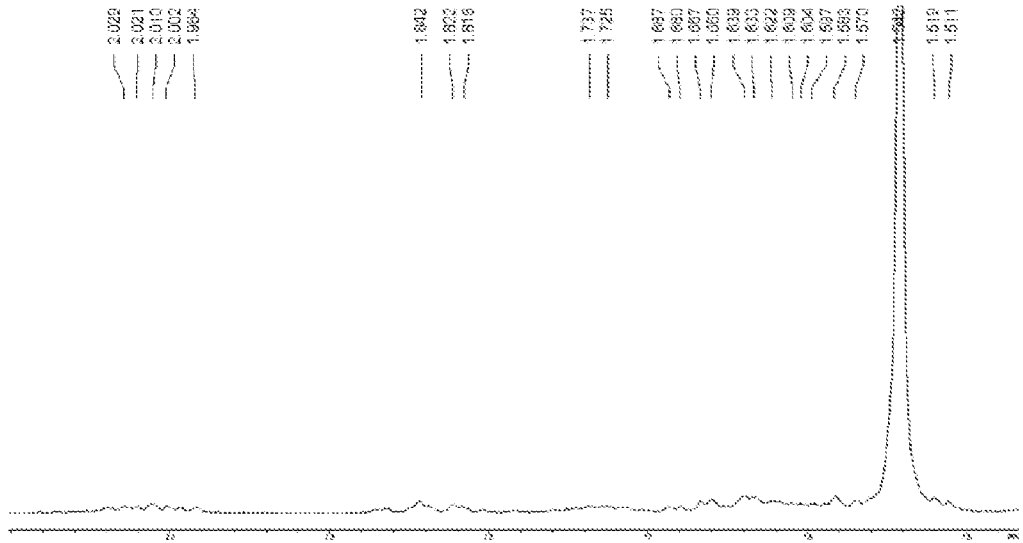
FIG. 9(E) shows $^1$H NMR data of 3 (CDCl$_3$).
Figure 9F:
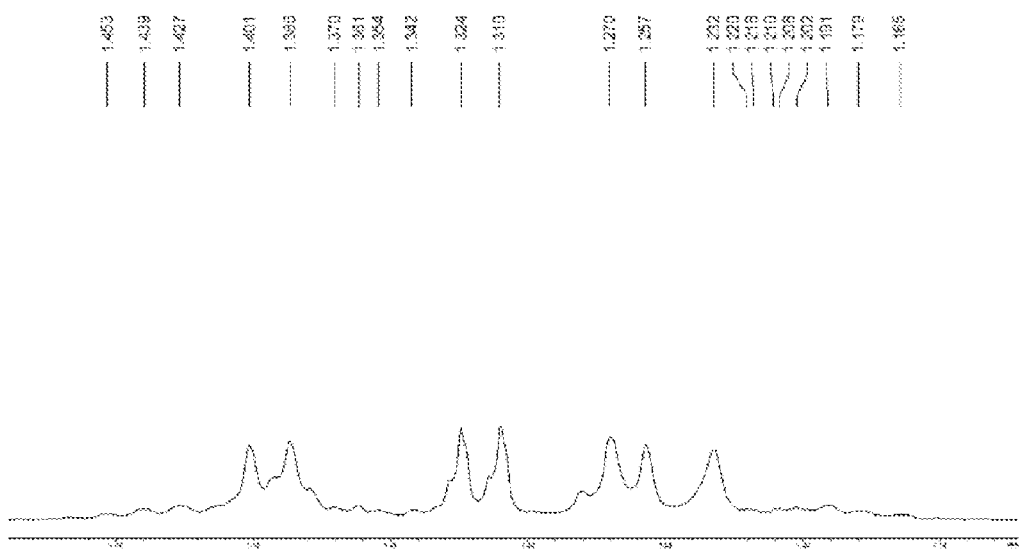
FIG. 9(F) shows $^1$H NMR data of 3 (CDCl$_3$).
Figure 9G:
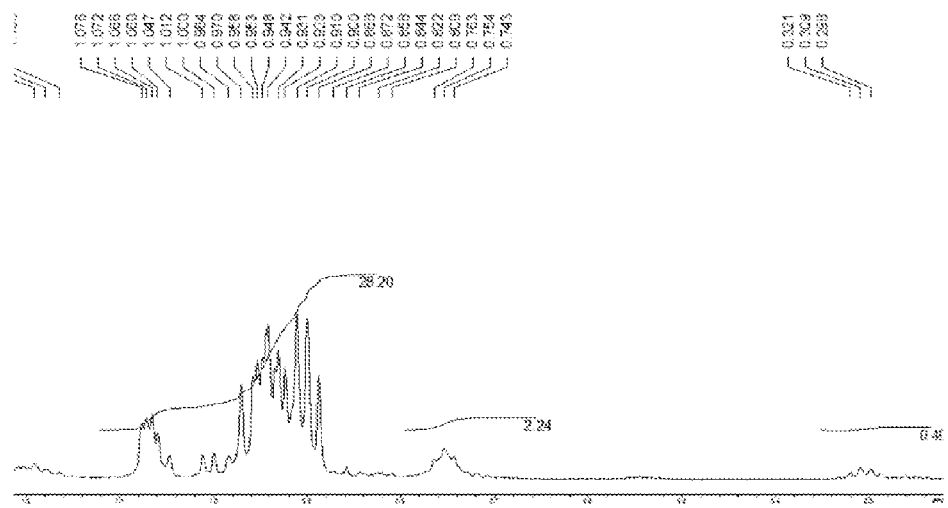
FIG. 9(G) shows $^1$H NMR data of 3 (CDCl$_3$).
Figure 10A:
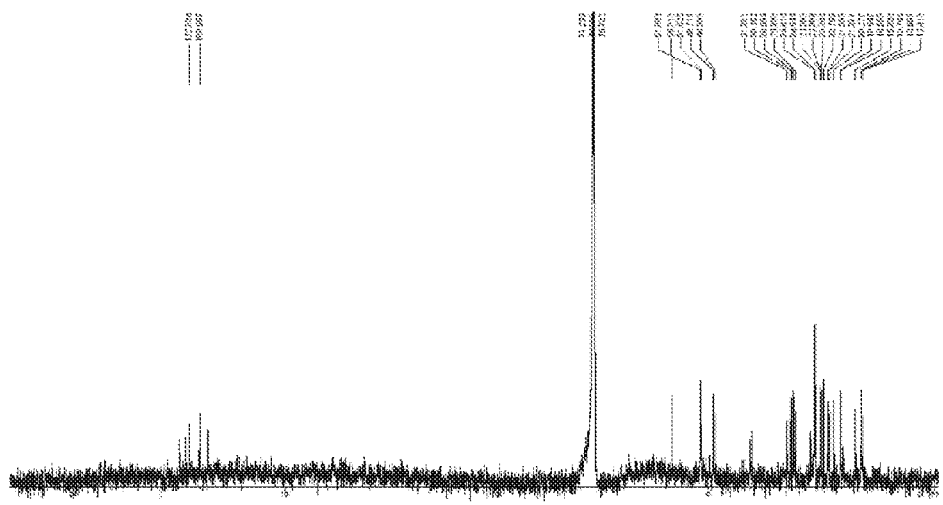
FIG. 10(A) shows $^{13}$C NMR data of 3 (CDCl$_3$).
Figure 10B:
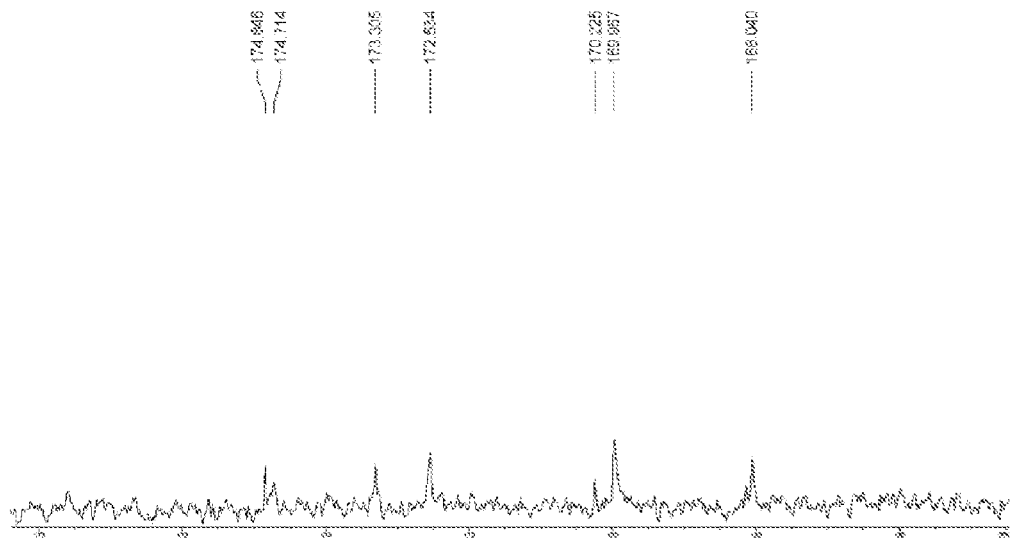
FIG. 10(B) shows $^{13}$C NMR data of 3 (CDCl$_3$).
Figure 10C:
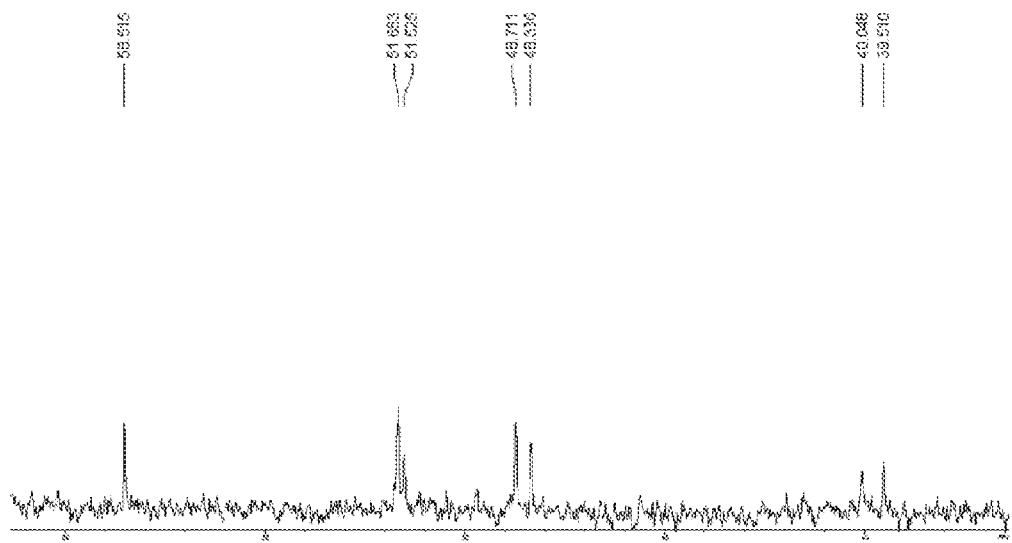
FIG. 10(C) shows $^{13}$C NMR data of 3 (CDCl$_3$).
Figure 10D:
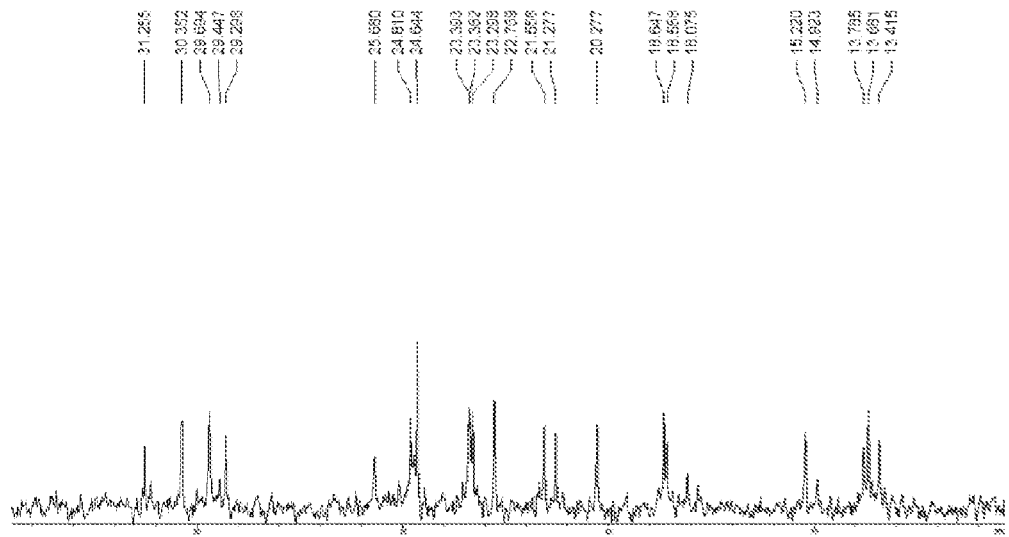
FIG. 10(D) shows $^{13}$C NMR data of 3 (CDCl$_3$).
Figure 11A:
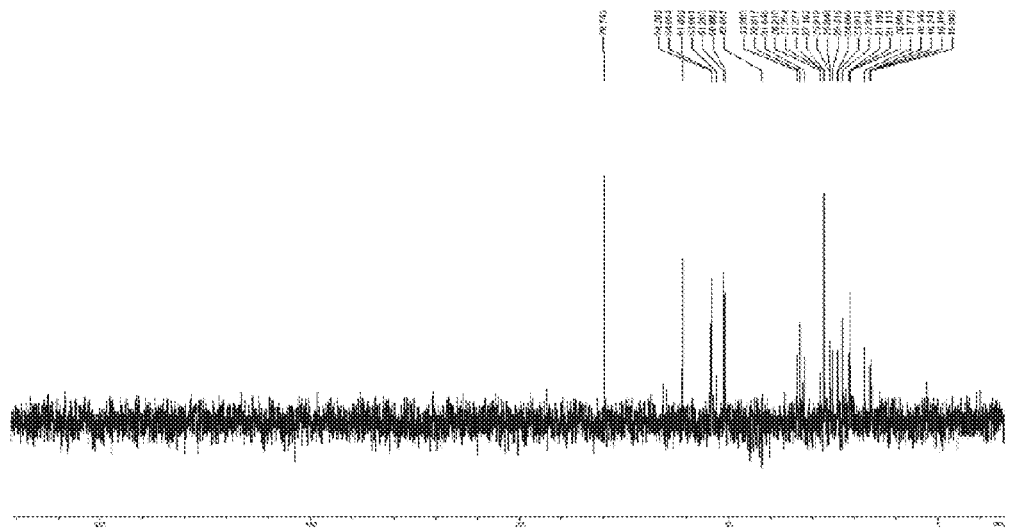
FIG. 11(A) shows DEPT-135 NMR data of 3 (CDCl$_3$).
Figure 11B:
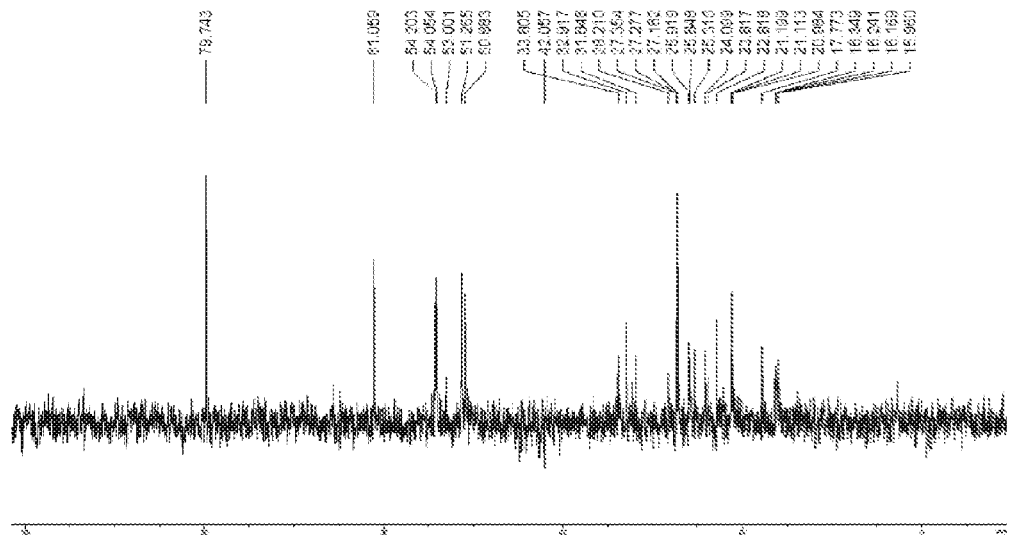
FIG. 11(B) shows DEPT-135 NMR data of 3 (CDCl$_3$).
Figure 12A:
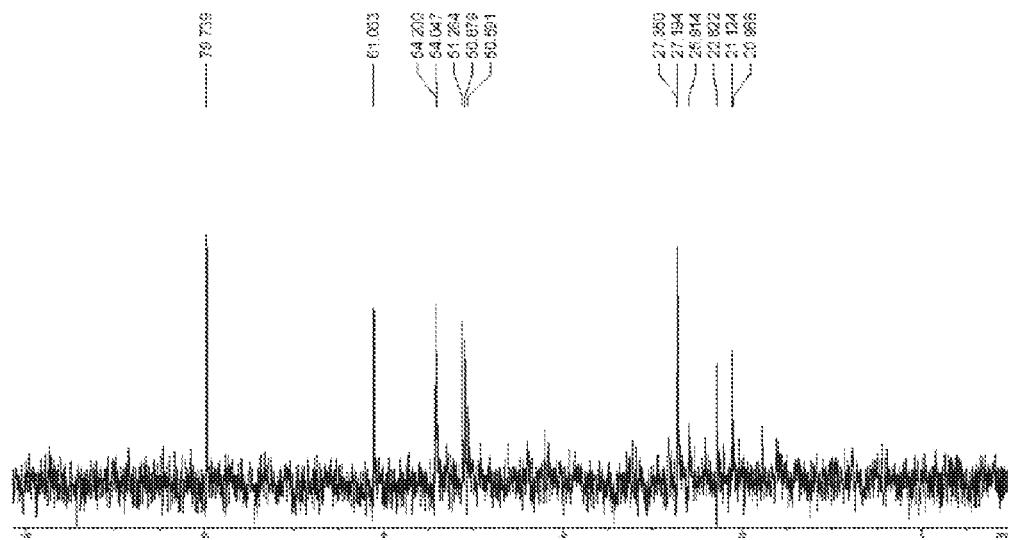
FIG. 12(A) shows DEPT-90 NMR data of 3 (CDCl$_3$).
Figure 12B:
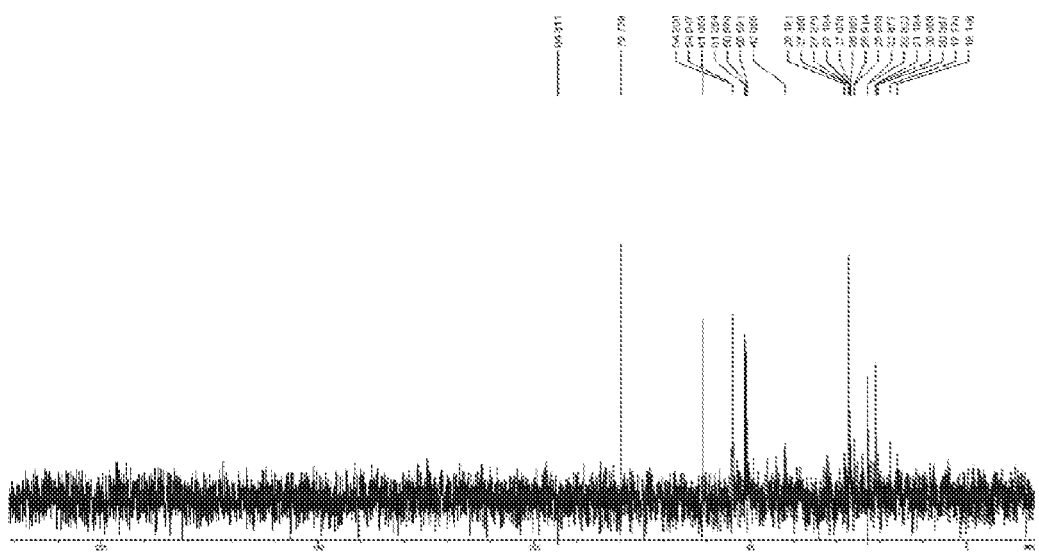
FIG. 12(B) shows DEPT-90 NMR data of 3 (CDCl$_3$).

Compound 3, [α]$_D^{20}$+0.4° (c 0.12, MeOH); was obtained as a white powder with a molecular formula of $C_{38}H_{68}N_7O_7$ by positive HRESIMS ([M+H]$^+$ m/z 734.5127, calcd. 734.5175) and NMR studies (Tables 4 and 5, and FIGS. 5(A)-5(F) and FIGS. 6(A)-6(D)). In combination of analysis 2D NMR data including $^1$H—$^1$H COSY, HMQC, HMBC, TOCSY and ROESY spectral data, the structure of compound 3 was determined as shown.

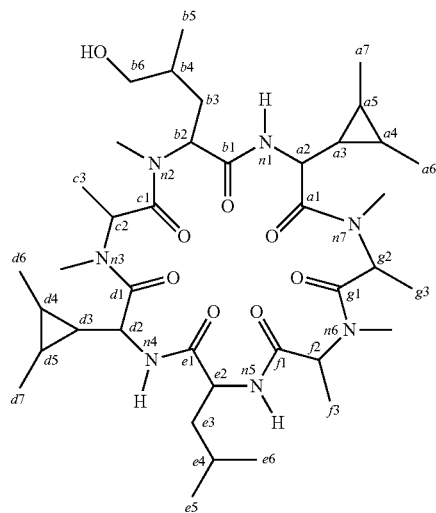

2

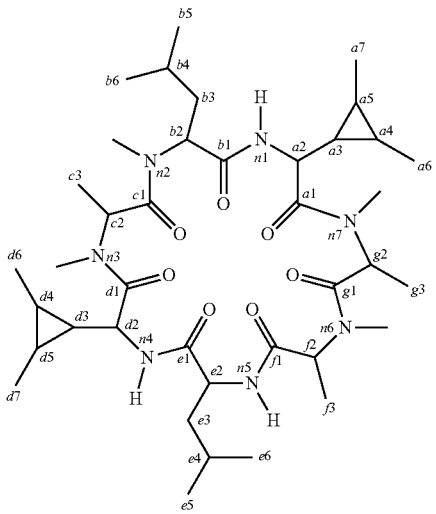

1

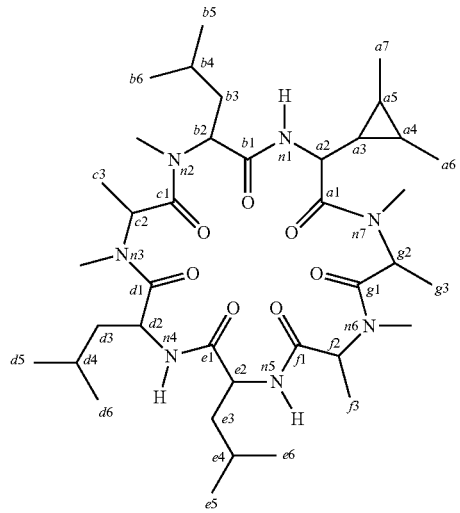

3

TABLE 4

| | $^1$H NMR Spectral Data of Compounds 1-3 (500 MHz; J in Hz; CDCl$_3$) | | |
|---|---|---|---|
| | 1 | 2 | 3 |
| Position | δ (ppm), multiplicity (coupling constant J in Hz) | | |
| | 1$^{st}$ Amino acid | | |
| H-a2 | 4.67 dd (8.8, 5.9) | 4.60 brdd (8.6, 5.7) | 4.68 brt (7.6) |
| H-a3 | 0.76 m | 0.84 m | 0.75 m |
| H-a4 | 0.25 sextet (5.5) | 0.23 sextet (5.3) | 0.30 br sextet (5.5) |
| H-a5 | 0.76 m | 0.78 sextet (5.5) | 0.75 m |
| CH$_3$-a6 | 0.92 d (5.9) | 0.93 d (5.9) | 0.87-0.98, overlap |
| CH$_3$-a7 | 1.06 d (5.5) | 1.03 d (5.9) | 1.07 d (5.9) |
| NH-n1 | 7.89 d (8.8) | 7.94 d (8.7) | 7.81 d (8.6) |
| | 2$^{nd}$ Amino acid | | |
| H-b2 | 4.19 brdd (9.8, 4.7) | 4.11 brdd (11.1, 3.1) | 4.30 m |
| H-b3a | 2.05 ddd (13.4, 10.2, 5.3) | 2.35 ddd (13.6, 11.6, 6.3) | 2.01 ddd (13.4, 9.2, 5.3) |
| H-b3b | 1.16 ddd (13.5, 8.1, 4.8) | 1.13 ddd (13.7, 7.9, 3.5) | 1.19 ddd (13.5, 8.7, 5.6) |
| H-b4 | 1.43br nonet (6.5) | 1.54 br nonet (6.3) | 1.44 br nontet (6.5) |
| CH$_3$-b5 | 0.95 d (6.6) | 0.98 d (6.9) | 0.87-0.98, overlap |
| H-b6a | | 3.42 dd (11.3, 4.9) | |
| H-b6b | | 3.31 dd (11.2, 5.6) | |

TABLE 4-continued

¹H NMR Spectral Data of Compounds 1-3 (500 MHz; J in Hz; CDCl₃)

| Position | 1 | 2 | 3 |
|---|---|---|---|
| | δ (ppm), multiplicity (coupling constant J in Hz) | | |
| $CH_3$-b6 | 0.89 d (6.6) | | 0.87-0.98, overlap |
| n2-$CH_3$ | 2.89 s | 2.88 s | 2.86 s |
| | | 3$^{rd}$ Amino acid | |
| H-c2 | 5.44 q (6.5) | 5.45 q (6.5) | 5.40 q (6.6) |
| $H_3$-c3 | 1.27 d (6.6) | 1.26 d (6.6) | 1.26 d (6.3) |
| n3-$CH_3$ | 3.06 s | 3.04 s | 3.07 s |
| | | 4$^{th}$ Amino acid | |
| H-d2 | 4.14 dd (10.3, 5.6) | 4.08 brdd (10.1, 5.2) | 4.77 m |
| H-d3 | 0.70 m | 0.72 m | |
| H-d3a | | | 1.58 m |
| H-d3b | | | 1.36 m |
| H-d4 | 0.54 sextet (5.5) | 0.56 sextet (5.5) | 1.73 m |
| H-d5 | 0.73 m | 0.72 m | |
| $CH_3$-d5 | | | 0.87-0.98, overlap |
| $CH_3$-d6 | 1.00 d (6.0) | 1.01 d (5.9) | 0.87-0.98, overlap |
| $CH_3$-d7 | 1.05 d (5.8) | 1.05 d (6.0) | |
| NH-n4 | 6.25 brs | 6.20 brd (4.7) | 6.24 brs |
| | | 5$^{th}$ Amino acid | |
| H-e2 | 4.47 brt (9.0) | 4.61 brt (10.0) | 4.24 m |
| H-e3a | 1.80 brt (10.1) | 1.76 brt (10.2) | 1.84 brt (10.3) |
| H-e3b | 1.64 m | 1.64 m | 1.66 m |
| H-e4 | 1.62 m | 1.62 m | 1.60 m |
| $CH_3$-e5 | 0.98 d (5.7) | 1.00 d (5.7) | 0.87-0.98, overlap |
| $CH_3$-e6 | 0.91 d (5.8) | 0.92 d (5.9) | 0.87-0.98, overlap |
| NH-n5 | 7.51 d (8.8) | 7.52 d (9.1) | 7.42 d (8.6) |
| | | 6$^{th}$ Amino acid | |
| H-f2 | 5.36 q (7.2) | 5.37 q (7.2) | 5.34 q (7.2) |
| $CH_3$-f3 | 1.32 d (7.2) | 1.33 d (7.2) | 1.32 d (7.2) |
| n6-$CH_3$ | 2.98 s | 2.97 s | 2.99 s |
| | | 7$^{th}$ Amino acid | |
| H-g2 | 4.89 q (7.3) | 4.92 q (7.4) | 4.86 q (7.3) |
| $CH_3$-g3 | 1.38 d (7.3) | 1.39 d (7.4) | 1.39 d (7.3) |
| n7-$CH_3$ | 3.16 s | 3.16 s | 3.16 s |

TABLE 5

¹³C NMR and DEPT Spectral Data of Compounds 1-3 (125 MHz; CDCl₃)

| Position | 1 | 2 | 3 |
|---|---|---|---|
| | δ (ppm), multiplicity | | |
| | 1$^{st}$ Amino acid | | |
| C-a1 | 173.50 s | 173.45 s | 173.32 s |
| C-a2 | 47.97 d | 48.28 d | 48.33 d |
| C-a3 | 24.79 d | 24.44 d | 25.80 d |
| C-a4 | 18.41 d | 18.52 d | 18.64 d |
| C-a5 | 20.27 d | 20.30 d | 20.27 d |
| C-a6 | 18.56 q | 18.52 q | 18.56 q |
| C-a7 | 13.63 q | 13.60 q | 13.79 q |
| | 2$^{nd}$ Amino acid | | |
| C-b1 | 168.08 s | 168.75 s | 168.05 s |
| C-b2 | 58.53 d | 58.72 d | 58.51 d |
| C-b3 | 39.85 t | 33.93 t | 39.50 t |
| C-b4 | 24.74 d | 33.09 d | 24.64 d |
| C-b5 | 21.69 q | 18.04 q | 21.55 q |
| C-b6 | 23.55 q | 66.52 t | 23.39 q |
| $CH_3$-n2 | 29.44 q | 29.55 q | 29.29 q |
| | 3$^{rd}$ Amino acid | | |
| C-c1 | 169.94 s | 169.68 s | 170.24 s |
| C-c2 | 49.69 d | 49.99 d | 48.71 d |
| C-c3 | 14.90 q | 14.84 q | 15.21 d |
| $CH_3$-n3 | 29.94 q | 29.94 q | 29.69 q |
| | 4$^{th}$ Amino acid | | |
| C-d1 | 172.24 s | 172.39 s | 172.54 s |
| C-d2 | 50.49 d | 50.62 d | 48.71 d |
| C-d3 | 25.20 d | 25.08 d | 40.05 t |
| C-d4 | 19.54 d | 19.57 d | 24.64 d |
| C-d5 | 17.79 d | 17.73 d | 21.27 q |
| C-d6 | 18.08 q | 18.04 q | 23.35 q |
| C-d7 | 13.19 q | 13.22 q | |
| | 5$^{th}$ Amino acid | | |
| C-e1 | 172.38 s | 172.51 s | 172.54 s |
| C-e2 | 51.05 d | 50.83 d | 51.65 d |
| C-e3 | 42.56 t | 43.15 t | 41.97 t |
| C-e4 | 24.98 d | 24.79 d | 24.80 d |
| C-e5 | 22.76 q | 21.70 q | 22.76 q |
| C-e6 | 23.37 q | 23.39 q | 23.29 q |
| | 6$^{th}$ Amino acid | | |
| C-f1 | 169.94 s | 169.96 | 169.97 s |
| C-f2 | 51.78 d | 51.86 d | 51.68 d |
| C-f3 | 13.63 q | 13.71 q | 13.41 q |
| $CH_3$-n6 | 30.39 q | 30.42 q | 30.36 q |

TABLE 5-continued $^{13}$C NMR and DEPT Spectral Data of
Compounds 1-3 (125 MHz; CDCl$_3$)

| Position | 1 | 2 | 3 |
|---|---|---|---|
| | δ (ppm), multiplicity | | |
| 7$^{th}$ Amino acid | | | |
| C-g1 | 174.70 s | 174.69 s | 174.85 s |
| C-g2 | 51.47 d | 51.47 d | 51.50 d |
| C-g3 | 13.63 q | 13.60 q | 13.68 q |
| CH$_3$-n7 | 31.09 q | 31.10 q | 31.25 q |

Cell Culture Panel Bioassays.

Pure compounds were evaluated against the human cancer cell lines comprising our cytotoxicity screening panel. Cytotoxicity assays involving oral epidermoid (KB), colon (HCT116), prostate (LNCaP), breast (MCF-7) and lung (A549) carcinoma cell lines, were performed using sulforhodamine B according to established protocols (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. J Med Chem 2006; 49: 693-708; and Jutiviboonsuk A, Zhang H J, Tan G T, Ma C M, Hung N V, Cuong N M, Bunyapraphatsara N, Soejarto D D, Fong H H S. Bioactive constituents from the roots of *Bursera tonkinensis*. Phytochemistry 2005; 66: 2745-2751.). All cell lines were purchased from the American Type Culture Collection (ATCC). KB cells were maintained in DMEM medium. LNCaP cells were maintained in RPMI1640 medium with hormone-free 10% heat-activated FBS (fetal bovine serum) supplemented with 0.1 nM testosterone. MCF-7 cells were maintained and assayed in MEME medium containing 10 mg/L of insulin. HCT116 cells were maintained in McCoy's 5A medium supplemented with 10% fetal bovine serum. A549 cells were maintained in RPMI-1640 medium supplemented with 10% FCS. Serial dilutions of the compounds were prepared using 10% aqueous DMSO as solvent. The 190 μL cell suspension ($3\times10^4$ cells in 1 ml media) was incubated with 10 μL sample solutions, in triplicate, in 96-well tissue culture plate at 37° C. in a humidified atmosphere of 5% CO$_2$ in air for 72 hours. 10 μL 10% aqueous DMSO was used as control group. Then the cells were fixed to plastic substratum by the addition of 100 μL cold 20% aqueous trichloroacetic acid and washing with water after incubation at 4° C. for 30 min. After staining cells with 100 μL of 0.4% sulforhodamine B in 1% aqueous AcOH for 30 min, unbound dye was removed by rinsing with 1% aqueous AcOH. The bound dye was solubilized with 200 μL 10 mM unbuffered Tris base, pH 10, and the optical density was measured at 515 nm using an ELISA plate reader. The average data were expressed as a percentage, relative to the control. The IC$_{50}$ values, the dose that inhibited cell growth by 50%, were calculated using non-linear regression analysis (percent survival versus concentration).

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and sub-combinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and sub-ranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A compound comprising formula (I) or formula (II):

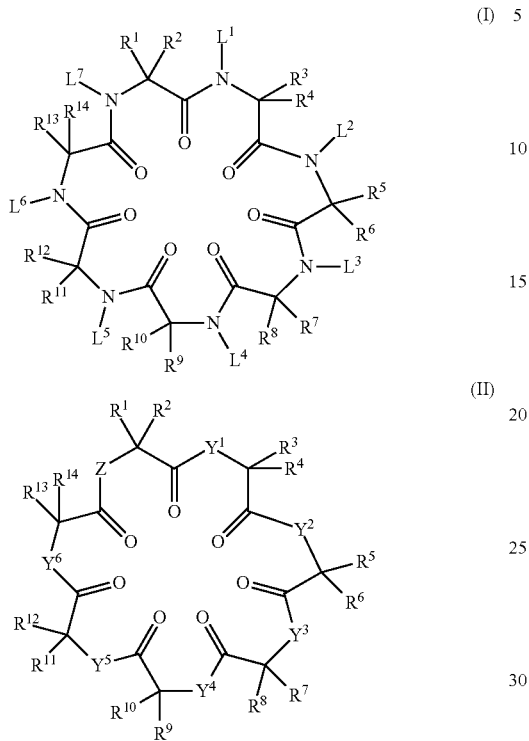

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from hydrogen, halogen and a moiety comprising 1 to 30 plural valence atoms selected from carbon, nitrogen, oxygen and sulphur;
at least one of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a cyclic group that contains 3 to 6 ring-forming atoms, and at least one of the ring-forming atoms is a methine (CH) carbon connecting to the ring of formula (I) or the ring of formula (II);
while one of $R^1$ and $R^2$, $R^3$ and $R^4$, $R^5$ and $R^6$, $R^7$ and $R^8$, $R^9$ and $R^{10}$, $R^{11}$ and $R^{12}$, or $R^{13}$ and $R^{14}$ is hydrogen, halogen, hydrocarbyl, alkoxy or cyclic group, the other one of $R^1$ and $R^2$, $R^3$ and $R^4$, $R^5$ and $R^6$, $R^7$ and $R^8$, $R^9$ and $R^{10}$, $R^{11}$ and $R^{12}$, or $R^{13}$ and $R^{14}$ is independently selected from $R^{15}$;
$R^{15}$ is independently selected from hydrogen, and hydrocarbyl optionally substituted with 1, 2, 3, 4 or 5 $R^{16}$;
$R^{16}$ is independently selected from halogen, —$OR^{17}$, —$C(O)R^{18}$, —$C(O)N(R^{17})R^{18}$, —$C(O)OR^{17}$, —$OC(O)R^{18}$, —$N(R^{17})R^{18}$, and —$N(R^{17})C(O)R^{18}$;
$R^{17}$ and $R^{18}$ are each independently hydrogen or hydrocarbyl;
$L^1$, $L^2$, $L^3$, $L^4$, $L^5$, $L^6$ and $L^7$ are each independently selected from hydrogen or hydrocarbyl, and at least two of $L^1$, $L^2$, $L^3$, $L^4$, $L^5$, $L^6$ and $L^7$ are hydrocarbyls;
Z is selected from oxygen, nitrogen, hydrocarbyl, or alkoxy;
$Y^1$, $Y^2$, $Y^3$, $Y^4$, $Y^5$ and $Y^6$ are each independently selected from nitrogen with substitution of an $L^1$, $L^2$, $L^3$, $L^4$, $L^5$ or $L^6$ group;
or an enantiomer thereof;
or a pharmaceutically acceptable salt or pro-drug thereof.

2. A compound selected from compound 1, compound 2 or compound 3:

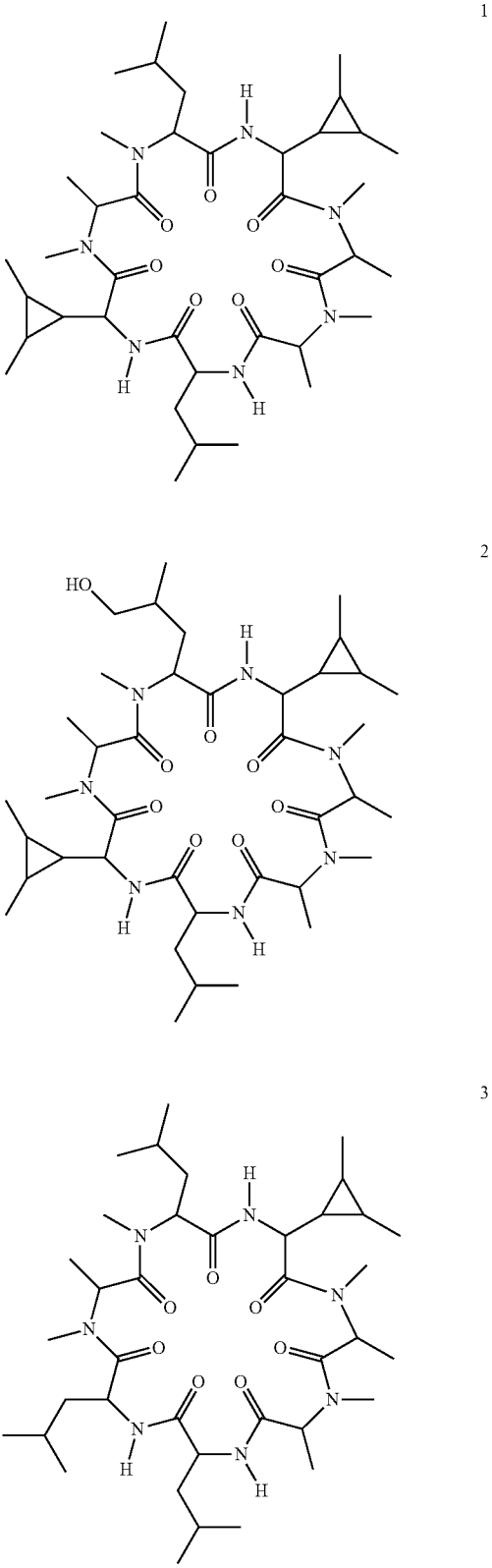

or a pharmaceutically acceptable salt or prodrug thereof.

3. A cyclic peptide comprising at least one substructure formed from an amino acid having formula (III):

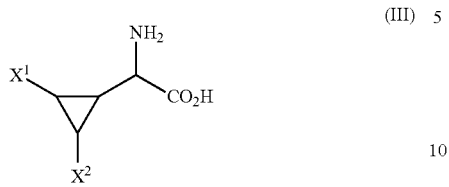

(III)

wherein:
$X^1$ and $X^2$ are each independently selected from R and $-OR^1$;
R is independently selected from halogen, and hydrocarbyl optionally substituted with 1, 2, 3, 4 or 5 $R^2$;
$R^1$ is independently selected from hydrogen, halogen, and hydrocarbyl optionally substituted with 1, 2, 3, 4 or 5 $R^2$;
$R^2$ is independently selected from halogen, $-OR^3$, $-C(O)R^4$, $-C(O)N(R^3)R^4$, $-C(O)OR^3$, $-OC(O)R^4$, $-N(R^3)R^4$, and $-N(R^3)N(R^3)R^4$;
$R^3$ and $R^4$ are each independently hydrogen or hydrocarbyl.

4. The cyclic peptide according to claim 3, wherein the cyclic peptide comprises an amide or an amine.

* * * * *